(12) United States Patent
Adkisson et al.

(10) Patent No.: US 7,273,756 B2
(45) Date of Patent: Sep. 25, 2007

(54) METHOD FOR CHONDROCYTE EXPANSION WITH PHENOTYPE RETENTION

(75) Inventors: Huston Davis Adkisson, St. Louis, MO (US); Curt L. Milliman, St. Louis, MO (US)

(73) Assignee: ISTO Technologies, Inc., St. Louis, MO (US)

( * ) Notice: Subject to any disclaimer, the term of this patent is extended or adjusted under 35 U.S.C. 154(b) by 207 days.

(21) Appl. No.: 10/956,971

(22) Filed: Oct. 1, 2004

(65) Prior Publication Data

US 2006/0073588 A1   Apr. 6, 2006

(51) Int. Cl.
*C12N 5/00* (2006.01)
(52) U.S. Cl. ............... 435/375; 435/325; 435/377; 435/378; 424/93.7
(58) Field of Classification Search ............. None
See application file for complete search history.

(56) References Cited

U.S. PATENT DOCUMENTS

| | | | |
|---|---|---|---|
| 4,356,261 A | | 10/1982 | Kuettner |
| 5,206,023 A | * | 4/1993 | Hunziker ............... 424/423 |
| 5,326,357 A | * | 7/1994 | Kandel ............... 623/23.72 |
| 5,658,582 A | | 8/1997 | Dorigatti et al. |
| 5,676,964 A | | 10/1997 | Della Valle et al. |
| 5,716,404 A | | 2/1998 | Vacanti et al. |
| 5,753,485 A | | 5/1998 | Dwulet et al. |
| 5,830,741 A | | 11/1998 | Dwulet et al. |
| 5,866,165 A | * | 2/1999 | Liu et al. ............... 424/486 |
| 5,948,692 A | * | 9/1999 | Miyauti et al. .......... 436/501 |
| 6,235,316 B1 | | 5/2001 | Adkisson |
| 6,251,876 B1 | | 6/2001 | Bellini et al. |
| 6,378,527 B1 | * | 4/2002 | Hungerford et al. ....... 128/898 |
| 6,582,960 B1 | | 6/2003 | Martin et al. |
| 6,617,161 B2 | | 9/2003 | Luyten et al. |
| 6,645,764 B1 | | 11/2003 | Adkisson |
| 2002/0076810 A1 | | 6/2002 | Radice et al. |
| 2003/0215426 A1 | | 11/2003 | French et al. |
| 2005/0036980 A1 | * | 2/2005 | Chaney et al. .......... 424/78.27 |

OTHER PUBLICATIONS

Girotto D et al. 2003. Tissue-specific gene expression in chondrocytes grown on three-dimensional hyaluronic acid scaffolds. Biomaterials 24: 3265-3275.*
Adkisson et al., "In Vitro Generation of Scaffold Independent Neocartilage," Clin. Orthopaedics and Related Res., 2001, pp. S280-S294, vol. 391S.
Benya et al., "Dedifferentiated Chondrocytes Reexpress the Differentiated Collagen Phenotype When Cultured in Agarose Gels," Cell, 1982, pp. 215-224, vol. 30.
Cima et al., "Hepatocyte Culture on Biodegradable Polymeric Substrates," Biotechnology and Bioengineering, 1991, pp. 145-158, vol. 38.

Cross-Linkers product literature, 2004, Rockford, Illinois, pp. 429-440.
De Bari et al., "Failure of In Vitro-Differentiated Mesenchymal Stem Cells from the Synovial Membrane to Form Ectopic Stable Cartilage in Vivo," Arthritis & Rheumatism, 2004, pp. 142-150, vol. 50.
De Bari et al., "Human Periosteum-Derived Cells Maintain Phenotypic Stability and Chondrogenic Potential Throughout Expansion Regardless of Donor Age," Arthritis & Rheumatism, 2001, pp. 85-95, vol. 44.
Dell'Accio et al., "Molecular Markers Predictive of the Capacity of Expanded Human Articular Chondrocytes to Form Stable Cartilage In Vivo," Arthritis & Rheumatism, pp. 1608-1619, vol. 44.
Farndale et al., "Improved Quantitation and Discrimination of Sulphated Glycosaminoglycans by Use of Dimethylmethylene Blue," Biochimica et Biophysica Acta, 1986, pp. 173-177, vol. 883.
Häuselmann et al., "Phenotypic Stability of Bovine Articular Chondrocytes After Long-Term Culture in Alginate Beads," J. Cell Sci., 1994, pp. 17-27, vol. 107.
Häuselmann et al., "Adult Human Chondrocytes Cultured in Alginate Form a Matrix Similar to Native Human Articular Cartilage," Am. J. Physiol., 1996, pp. C742-C752, vol. 271.
Hermanson, GT Bioconjugate Techniques, 1996, San Diego, Academic Press, Inc., p. 622.
Homicz et al., "Effects of Serial Expansion of Septal Chondrocytes on Tissue-Engineered Neocartilage Composition," Otolaryngol. Head Neck Surg., 2002, pp. 398-408, vol. 127.
Huang et al., "Chondrogenic Potential of Multipotential Cells from Human Adipose Tissue," Plast. Reconstr. Surg., 2004, pp. 585-594, vol. 113.
Hunziker, "Articular Cartilage Repair: Basic Science and Clinical Progress. A Review of the Current Status and Prospects," Osteoarthritis and Cartilage, 2001, pp. 432-463, vol. 10.
Jakob et al, Specific Growth Factors During the Expansion and Redifferentiation of Adult Human Articular Chondrocytes Enhance Chondrogenesis and Cartilaginous Tissue Formation in Vitro, J. Cell. Biochem., 2001, pp. 368-377, vol. 81.

(Continued)

*Primary Examiner*—Sandra E. Saucier
*Assistant Examiner*—Lora E Barnhart
(74) *Attorney, Agent, or Firm*—Biotactica, LLC

(57) ABSTRACT

The present invention provides a method that maintains chondrocyte phenotype during serial expansion by culturing a population of chondrocytes in a defined serum-free culture medium containing cytokines and on a substrate that is modified by covalent attachment of hyaluronic acid. The underlying principle is to maintain native chondrocyte phenotype by growing the dissociated chondrocytes on a substrate modified by covalent attachment of hyaluronic acid to retain native chondrocyte morphology and function. Chondrocyte expanded in this manner can be used in various medical applications to repair cartilaginous tissues that have been injured by trauma or disease. This substratum provides a microenvironment that more closely mimics that of native articular cartilage, thereby promoting chondrogenesis in a predictable manner.

16 Claims, 11 Drawing Sheets

OTHER PUBLICATIONS

Kavalkovich et al., "Chondrogenic Differentiation of Human Mesenchymal Stem Cells Within an Alginate Layer Culture System," In Vitro Cell Dev. Biol.—Animal, 2002, pp. 457-466, vol. 38.

Kögler et al., "A New Human Somatic Stem Cell form Placental Cord Blood with Intrinsic Pluripotent Differentiation Potential," J. Exp. Med., 2004, pp. 123-135, vol. 200.

Kujawa et al., "Hyaluronic Acid Bonded to Cell Culture Surfaces Inhibits the Program of Myogenesis," Developmental Biol., 1986 pp. 10-16, vol. 113

Kujawa et al., "Substrate-Bonded Hyaluronic Acid Exhibits a Size-Dependent Stimulation of Chondrogenic Differentiation of Stage 24 Limb Mesenchymal Cells in Culture," Development Biol., 1986, pp. 519-528, vol. 114.

Kujawa et al., "Hyaluronic Acid Bonded to Cell-Culture Surfaces Stimulated Chondrogenesis in Stage 24 Limb Mesenchyme Cell Cultures," Developmental Biol., 1986, pp. 504-518, vol. 114.

Laurent et al., "Hyaluronan," FASEB J., 1992, pp. 2397-2404, vol. 6.

Laurent, "Structure of Hyaluronic Acid," in the Chemistry and Molecular Biology of the Intercellular Matrix, 1970, (Balazs ed., Academic Press, New York), pp. 703-732, vol. 2.

Liu et al., "An Osteoconductive Collagen/Hyaluronate Matrix for Bone Regeneration," Biomaterials, 1999, pp. 1097-1108, vol. 20.

Mackay et al., "Chondrogenic Differentiation of Cultured Human Mesenchymal Stem Cells from Marrow," Tissue Engineering, 1998, pp. 415-428, vol. 4.

Malpeli et al., "Serum-Free Growth Medium Sustains Commitment of Human Articular Chondrocyte Through Maintenance of Sox9 Expression," Tissue Engineering, 2004, pp. 145-155, vol. 10.

Mandl et al., "Serum-Free Medium Supplemented with High-Concentration FGF2 for Cell Expansion-Culture of Human Ear Chondrocytes Promotes Redifferentiation Capacity," Tissue Engineering, 2002, pp. 573-580, vol. 8.

Mandl et al., "Multiplication of Human Chondrocytes with Low Seeding Densities Accelerates Cell Yield Without Losing Redifferentiation Capacity," Tissue Engineering, 2004, pp. 109-118, vol. 10.

Ornitz et al., "Fibroblast Growth Factors," Genome Biol., 2001, pp. 1-12, vol. 2.

Ornitz, "FGFs, Heparan Sulfate and FGFRs: Complex Interactions Essential for Development," BioEssays, 2000, pp. 108-112, vol. 22.

Osman et al., "Combined Transgenic Expression of a α-Galactosidase and α1,2-Fucosyltransferase Leads to Optimal Reduction in the Major Xenoepitope Galα(1,3)Gal," Proc. Natl. Acad. Sci. USA, 1997, pp. 14677-14682, vol. 94.

Plotnikov et al., "Crystal Structures of Two FGF-FGFR Complexes Reveal the Determinants of Ligand-Receptor Specificity," Cell, 2000, pp. 413-424, vol. 101.

Reginato et al., "Formation of Nodular Structures Resembling Mature Articular Cartilage in Long-Term Primary Cultures of Human Fetal Epiphyseal Chondrocytes on a Hydrogel Substrate," Arthritis & Rheumatism, 1994, pp. 1338-1349, vol. 37.

Sandrin et al., "Enzymatic Remodelling of the Carbohydrate Surface of a Xenogenic Cell Substantially Reduces Human Antibody Binding and Complement-Mediated Cytolysis," Nature medicine, 1995, pp. 1261-1267, vol. 1.

Sekiya et al., "Dexamethasone Enhances SOX9 Expression in Chondrocytes," J. Endocrinol., 2001, pp. 573-579, vol. 169.

Singley et al., "The Spatial Distribution of Hyaluronic Acid and Mesenchymal Condensation in the Embryonic Chick Wing," Dev. Biol., 1981, pp. 102-120, vol. 84.

Stegemann et al., "Determination of Hydroxyproline," Clinica Chemica Acta, 1967, pp. 267-273, vol. 18.

Turley et al., "Spontaneous Glycosylation of Glycosaminoglycan Substrates by Adherent Fibroblasts," Cell, 1979, pp. 109-115, vol. 17.

Vacanti et al., "Beyond Transplantation—Third Annual Samuel Jason Mixter Lecture," Arch. Surg., 1988, pp. 545-549, vol. 123.

Vacanti et al., "Selective Cell Transplantation Using Bioabsorbable Artificial Polymers as Matrices," J. Pediatric Surg., 1988, pp. 3-9, vol. 23.

West et al., "Angiogenesis Induced by Degradation Products of Hyaluronic Acid," Science, 1985, pp. 1324-1326, vol. 228.

Yoon et al., "Maintenance of Differentiated Phenotype of Articular Chondrocytes by Protein C and Extracellular Signal-Regulated Protein Kinase," J. Biol. Chem., 2002, pp. 8412-8420, vol. 277.

Barbero et al., Osteoarthritis Cartilage 12: 476-484, 2004.

Aigner et al., J. Biomed. Mater. Res., 1998, pp. 172-181, vol. 42.

Bradham et al., Clin. Ortho. Rel. Res., 1998, pp. 239-249, vol. 352.

Ehlers et al., Annals Anat., 2001, pp. 13-17, vol. 183.

Hegewald et al., Tissue Cell, 2004, pp. 431-438, vol. 36.

* cited by examiner

14 Month-old
Freshly isolated

14 Month-old
Passage 2
6.5 population
doublings

SEQUENCE LISTING

```
<160> NUMBER OF SEQ ID NOS: 22

<210> SEQ ID NO 1
<211> LENGTH: 23
<212> TYPE: DNA
<213> ORGANISM: Artificial
<220> FEATURE:
<223> OTHER INFORMATION: AGC1-2S primer, Aggrecan core, GenBank ID No.
      NM_01135

<400> SEQUENCE: 1
gaaacttcag accatgacaa ctc                                             23

<210> SEQ ID NO 2
<211> LENGTH: 21
<212> TYPE: DNA
<213> ORGANISM: Artificial
<220> FEATURE:
<223> OTHER INFORMATION: AGC1-2AS primer, Aggrecan core, GenBank ID No.
      NM_01135

<400> SEQUENCE: 2
accagcagca ctacctcctt c                                               21

<210> SEQ ID NO 3
<211> LENGTH: 20
<212> TYPE: DNA
<213> ORGANISM: Artificial
<220> FEATURE:
<223> OTHER INFORMATION: B7-H1-1S primer, B7-H1, GenBank ID No.
      NM_014143

<400> SEQUENCE: 3
gctcttggtg ctggctggtc                                                 20

<210> SEQ ID NO 4
<211> LENGTH: 23
<212> TYPE: DNA
```

```
<213> ORGANISM: Artificial
<220> FEATURE:
<223> OTHER INFORMATION: B7-H1-1AS primer, B7-H1, GenBank ID No.
      NM_014143

<400> SEQUENCE: 4
tcagatatac taggtgtagg gaa                                            23

<210> SEQ ID NO 5
<211> LENGTH: 24
<212> TYPE: DNA
<213> ORGANISM: Artificial
<220> FEATURE:
<223> OTHER INFORMATION: B7-1-6S primer, B7-1, GenBank ID No. NM_005191

<400> SEQUENCE: 5
gccatcaaca caacagtttc ccaa                                           24

<210> SEQ ID NO 6
<211> LENGTH: 25
<212> TYPE: DNA
<213> ORGANISM: Artificial
<220> FEATURE:
<223> OTHER INFORMATION: B7-1-6AS primer, B7-1 (CD80), GenBank ID No.
      NM_005191

<400> SEQUENCE: 6
cagggcgtac actttcccctt ctcaa                                         25

<210> SEQ ID NO 7
<211> LENGTH: 23
<212> TYPE: DNA
<213> ORGANISM: Artificial
<220> FEATURE:
<223> OTHER INFORMATION: B7-2-6S primer, B7-2, GenBank ID No. NM_006889

<400> SEQUENCE: 7
ctctctggtg ctgctcctct gaa                                            23

<210> SEQ ID NO 8
<211> LENGTH: 27
<212> TYPE: DNA
<213> ORGANISM: Artificial
<220> FEATURE:
<223> OTHER INFORMATION: B7-1-6AS primer, B7-2 (CD86), GenBank ID No.
      NM_006889

<400> SEQUENCE: 8
ctgtgggctt tttgtgatgg atgatac                                        27

<210> SEQ ID NO 9
<211> LENGTH: 20
<212> TYPE: DNA
<213> ORGANISM: Artificial
<220> FEATURE:
<223> OTHER INFORMATION: CollA1-3S primer, CollA1, GenBank ID No.
      NM_000088

<400> SEQUENCE: 9
cgagggccaa gacgaagaca                                                20

<210> SEQ ID NO 10
<211> LENGTH: 22
<212> TYPE: DNA
<213> ORGANISM: Artificial
<220> FEATURE:
<223> OTHER INFORMATION: CollA1-3AS primer, CollA1, GenBank ID No.
```

NM_000088

<400> SEQUENCE: 10
cttggtcggt gggtgactct ga                                          22

<210> SEQ ID NO 11
<211> LENGTH: 26
<212> TYPE: DNA
<213> ORGANISM: Artificial
<220> FEATURE:
<223> OTHER INFORMATION: Col2A1-8S primer, Col2A1, GenBank ID No.
      NM_033150

<400> SEQUENCE: 11
caccctgagt ggaagagtgg agctac                                      26

<210> SEQ ID NO 12
<211> LENGTH: 23
<212> TYPE: DNA
<213> ORGANISM: Artificial
<220> FEATURE:
<223> OTHER INFORMATION: Col2A1-8AS primer, Col2A1, GenBank ID No.
      NM_033150

<400> SEQUENCE: 12
cagtgttggg agccagattg tca                                         23

<210> SEQ ID NO 13
<211> LENGTH: 27
<212> TYPE: DNA
<213> ORGANISM: Artificial
<220> FEATURE:
<223> OTHER INFORMATION: Col9A1-5S primer, Col9A1, GenBank ID No. X54412

<400> SEQUENCE: 13
aagcacaact cagtgcccca acaaaac                                     27

<210> SEQ ID NO 14
<211> LENGTH: 20
<212> TYPE: DNA
<213> ORGANISM: Artificial
<220> FEATURE:
<223> OTHER INFORMATION: Col9A1-6AS primer, Col9A1, GenBank ID No.
      X54412

<400> SEQUENCE: 14
atcccatcac ggccatcaca                                             20

<210> SEQ ID NO 15
<211> LENGTH: 27
<212> TYPE: DNA
<213> ORGANISM: Artificial
<220> FEATURE:
<223> OTHER INFORMATION: Col11A1-2S primer, Col11A1, GenBank ID No.
      J04177

<400> SEQUENCE: 15
aagcacaact cagtgcccca acaaaac                                     27

<210> SEQ ID NO 16
<211> LENGTH: 24
<212> TYPE: DNA
<213> ORGANISM: Artificial
<220> FEATURE:
<223> OTHER INFORMATION: Col11A1-2AS primer, Col11A1, GenBank ID No.
      J04177

```
<400> SEQUENCE: 16
ctacccgatg ccacttcccg tcag                                              24

<210> SEQ ID NO 17
<211> LENGTH: 21
<212> TYPE: DNA
<213> ORGANISM: Artificial
<220> FEATURE:
<223> OTHER INFORMATION: GAPDH-1S primer, GAPDH, GenBank ID No.
      NM_002046

<400> SEQUENCE: 17
gcaaattcca tggcaccgtc a                                                 21

<210> SEQ ID NO 18
<211> LENGTH: 20
<212> TYPE: DNA
<213> ORGANISM: Artificial
<220> FEATURE:
<223> OTHER INFORMATION: GAPDH-1AS primer, GAPDH, GenBank ID No.
      NM_002046

<400> SEQUENCE: 18 cagggtgct aagcagttgg                                                    20

<210> SEQ ID NO 19
<211> LENGTH: 26
<212> TYPE: DNA
<213> ORGANISM: Artificial
<220> FEATURE:
<223> OTHER INFORMATION: NCAD-1S primer, N-cadherin, GenBank ID No.
      BC036470

<400> SEQUENCE: 19
ggaaaagtgg caagtggcag taaaat                                            26

<210> SEQ ID NO 20
<211> LENGTH: 26
<212> TYPE: DNA
<213> ORGANISM: Artificial
<220> FEATURE:
<223> OTHER INFORMATION: NCAD-1AS primer, N-cadherin, GenBank ID No.
      BC036470

<400> SEQUENCE: 20
ccgagatggg gttgataatg aagata                                            26

<210> SEQ ID NO 21
<211> LENGTH: 23
<212> TYPE: DNA
<213> ORGANISM: Artificial
<220> FEATURE:
<223> OTHER INFORMATION: SOX9-1S primer, SOX-9, GenBank ID No. Z46629

<400> SEQUENCE: 21
gtcaacggct ccagcaagaa caa                                               23

<210> SEQ ID NO 22
<211> LENGTH: 19
<212> TYPE: DNA
<213> ORGANISM: Artificial
```

```
<220> FEATURE:
<223> OTHER INFORMATION: SOX9-1AS primer, SOX-9, GenBank ID No. Z46629

<400> SEQUENCE: 22
gctccgcctc ctccacgaa                                                    19
```

METHOD FOR CHONDROCYTE EXPANSION WITH PHENOTYPE RETENTION

STATEMENT REGARDING FEDERALLY SPONSORED RESEARCH OR DEVELOPMENT

Research relating to the invention was supported in part by a NIST sponsored ATP Award 70NANB1H3027 The Government has certain rights to paid up, royalty-free non-exclusive license of the invention.

CROSS-REFERENCE TO RELATED APPLICATIONS

Not applicable.

REFERENCE TO A SEQUENCE LISTING

The Sequence Listing, which is a part of the present disclosure, includes a text file comprising primer nucleotide and/or amino acid sequences of the present invention on a compact disc. The subject matter of the Sequence Listing is incorporated herein by reference in its entirety.

BACKGROUND OF THE INVENTION

Millions of people in the United States alone are afflicted with painful inflammatory or degenerative arthritis which limits normal joint function and results in loss of quality of life. The primary cause of degenerative arthritis is breakdown of the cartilage matrix. Cartilage is a smooth, flexible connective tissue covering the ends of a joint which functions to cushion the bone and allow the joint to move easily without pain. Loss of joint articular cartilage due to traumatic injury or disease ultimately results in joint stiffening caused by "bone on bone movement" and painful exposure of nerve endings in subchondral bone.

In mammals, cartilage contributes to the structure of several organs and systems like the articular surface of joints and other joint-associated structures, including the ear, the nose, the larynx, the trachea, the bronchi, structures of the heart valves, etc. There are different types of cartilage in mammals: fibro-cartilage, elastic cartilage and hyaline cartilage. Fibro-cartilage contains an abundance of type I collagen and is found in the intervertebral disks and ligaments. Elastic cartilage contains elastin fibrils and is found in the pinna of the ear and in the epiglottis. Hyaline cartilage, a semi-transparent and clear cartilage tissue found in the cartilagenous walls of the trachea and bronchia, the costal cartilage and growth plate, as well as in cartilage of the nose, larynx and diarthroidal joints, contains neither type I collagen nor elastin. Hyaline cartilage having a distinctive combination of cartilage-specific collagens (types II, VI, IX, and XI) and aggregating proteoglycans (aggrecan) that give it the unique ability to withstand compressive forces is called articular cartilage.

Damage to articular cartilage results in lesions of the joint surface, and progressive degeneration of these lesions often leads to symptomatic joint pain, disability and reduced or disturbed functionality. Joint surface defects can be the result of various aetiologies, including inflammatory processes, neoplasias, post-traumatic and degenerative events, etc. Adult articular cartilage has a major shortcoming: unlike most tissues, it cannot repair itself. Lack of a blood supply in large part restricts the tissue's ability to recruit chondro-progenitor cells that can act to repair articular cartilage defects. Consequently, articular cartilage defects that have progressed to advanced degenerative disease require total joint arthroplasty to eliminate pain and to restore normal joint function.

Tissue-engineered growth of articular cartilage represents a biologic solution which may delay or reduce the need for metal- and polymer-based materials currently used in total joint arthroplasty. Several biologic approaches have attempted to repair or regenerate articular cartilage that is damaged by trauma or disease (Hunziker, 2003). The majority of these approaches combine cell-based therapy with biodegradable polymers to create a three-dimensional construct that can be transplanted into the knee. However, these experimental therapies have not produced long-lasting repair of hyaline cartilage (Buckwatler et al., 1990; Hunziker, 2002).

One technique that has gained FDA approval for cartilage repair is Autologous Chondrocyte Implantation (Carticel, Genzyme Surgery). In this procedure, a small tissue biopsy obtained from the patient's joint articular cartilage is taken to the lab where chondrocytes (cartilage cells) are isolated and expanded ex vivo for subsequent re-implantation into the patient in a second surgical procedure. A key limitation of this method is the relatively small number of donor cells that can be obtained at biopsy, and chondrocytes derived from adult articular cartilage appear to have a limited ability to produce cartilage matrix after expansion.

A successful tissue engineered approach to cartilage repair must make use of cells that can be expanded in a scalable process that is both efficient and reproducible and which retains the ability of the expanded chondrocytes to synthesize functional cartilage for use in transplantation. Currently, the most widely used technique for chondrocyte expansion is monolayer culture (U.S. Pat. No. 4,356,261). However, chondrocytes grown in monolayer culture using serum-containing medium undergo a process of dedifferentiation in which chondrocytes lose their spherical shape and acquire an elongated fibroblastic morphology. Biochemical changes associated with loss of native chondrocyte shape include arrested synthesis of cartilage-specific collagens and proteoglycans, subsequent initiation of type I and III collagen synthesis and increased synthesis of small non-aggregating proteoglycans.

Loss of chondrocyte phenotype during serial expansion in vitro poses a key limitation to the commercialization of orthobiologic approaches to articular cartilage repair. To counter dedifferentiation, chondrocytes traditionally have been suspended in three-dimensional environments such as hydrogels, e.g., agarose (Benya and Shafer, 1982) or alginate (Hauselmann et al., 1994 and 1996), pellet culture (Mackay et al., 1998; Jakob et al., 2001; Barbero et al., 2004), or three-dimensional scaffolds (Vacanti et al., 1998). Chondrocytes are reported to better retain their native rounded morphologic appearance and to synthesize macromolecules characteristic of hyaline cartilage when maintained in three-dimensional suspension culture after expansion. However, many of such cultured chondrocytes still produce type I collagen and small proteoglycans, indicating an "incompletely" restored cartilage phenotype. Furthermore, the potential for carry over of residual materials derived from the three-dimensional hydrogels can complicate the regulatory path. Alginate, for example, is reported to induce inflammation and may be cytotoxic when used in vivo.

A logical approach to retain chondrocyte phenotype during in vitro expansion would be to recapitulate the in vivo microenvironment to which chondrocytes are naturally exposed during embryonic development. Therefore, matrices such as type II and VI collagen or aggregating proteoglycans may serve as excellent substrata for chondrocyte expansion and growth, particularly in the absence of serum-derived factors.

During embryonic development, condensation and proliferation of mesenchymal progenitor cells forms the cartilage anlagen through a process known as chondrogenesis. Further differentiation of the cartilage template results in formation of joint articular cartilage and bone. Many factors are believed to play a critical role in chondrogenesis, including the extracellular matrix, growth and differentiation factors, their antagonists as well as specific cell surface membrane receptors including, N-cadherin, bone morphogenetic protein receptor type 1A (BMPR-1A) and bone morphogenetic protein receptor type 1B (BMPR-1B).

An important component of the extracellular matrix, hyaluronic acid (HA) plays a critical role in cartilage development and in the maintenance of tissue homeostasis. HA is a non-sulfated, linear glycosaminoglycan of the extracellular matrix consisting of repeating units of($\beta$, 1-4) D-glucuronic acid-($\beta$1-3)—N-acetyl-D-glucosamine (Laurent, 1970). HA is ubiquitously distributed in body tissues and has been shown to play an important role in a number of biological processes including embryonic development, wound healing and tumor growth by providing a provisional matrix that supports cellular migration, adherence, proliferation and differentiation (Laurent and Fraser, 1992). In its native state, HA exists as a high molecular weight polymer, usually in excess of $1\times10^6$ daltons. However, during morphogenesis, inflammation and tissue repair reduced molecular weight forms are generated by proteolytic cleavage. Hyaluronic acid of intermediate molecular weight (200,000 to 400,000) is reported to promote differentiation of chondrogenic progenitor cells (Kujawa et al., 1986 A and 1986B), whereas HA of reduced MW promotes angiogenesis (West et al., 1985). Such findings have led to the commercial development of HA-based scaffolds for tissue engineered growth of cartilage and bone, as a means of regenerating tissues that have been destroyed by trauma or disease (Campoccia et al., 1998 U.S. Pat. Nos. 6,251,876; 5,676,964; 5,658, 582).

SUMMARY OF THE INVENTION

In one aspect, the present invention provides a method for expanding a population of cells by culturing a population of cells in vivo in a culture medium containing at least one cytokine on a substrate having a surface modified with hyaluronic acid; and maintaining the cells on the substrate for a sufficient time to allow at least one doubling of the cell population. The substrate is modified by covalently attaching hyaluronic acid by a cross-linking agent, preferably a carbodiimide. Alternatively, it is contemplated that cross-linking of HA to a reactive sulfonamide (derivative of polystyrene) is achieved using a reactive aldehyde created by the oxidation of HA (Liu et al., 2003). Preferably, the substrate is virgin polystyrene, although other forms of tissue culture plastic can be used. The chondrocytes are selected from cartilagenous tissue that is isolated from either juveniles or adults. Additional sources of chondroprogenitor cells include, without limitation, mesenchymal stem cells, cartilage cells, umbilical cord stem cells, bone marrow stromal cells, adipose stromal cells or chondrogenic progenitor cells derived from periosteum or synovium.

The present invention is also directed to methods of generating cells suitable for cartilage repair by expanding chondrocytes and retaining the phenotype of the expanded chondrocytes by culturing the chondrocytes in a cytokine medium on a substrate to which hyaluronic acid is covalently bound.

In yet another aspect of the present invention, a method is provided for maintaining native chondrocyte phenotype in dividing cells by culturing chondrocytes in a cytokine culture medium on a substrate modified with hyaluronic acid in which the substrate provides a scaffold for the chondrocytes to expand and retain the chondrocyte phenotype.

The present invention also provides a kit for generating cells for cartilage repair, the kit comprises a culture medium containing at least one cytokine; and a substrate modified with hyaluronic acid.

Another embodiment of the present invention is a method for generating cartilage cells that are suitable for tissue implantation by retaining chondrocyte phenotype during in vitro expansion. Preferably, the tissue implanted is cartilage or cartilaginous.

S-GAG, sulfated glycosaminoglycan; DNA, deoxyribose nucleic acid. DMEM, Dulbecco's modified Eagle's medium; LG, low glucose; HL, HL-1™ Complete Serum Free Medium manufactured by Cambrex, Walkersville, Md.

Figure 2:
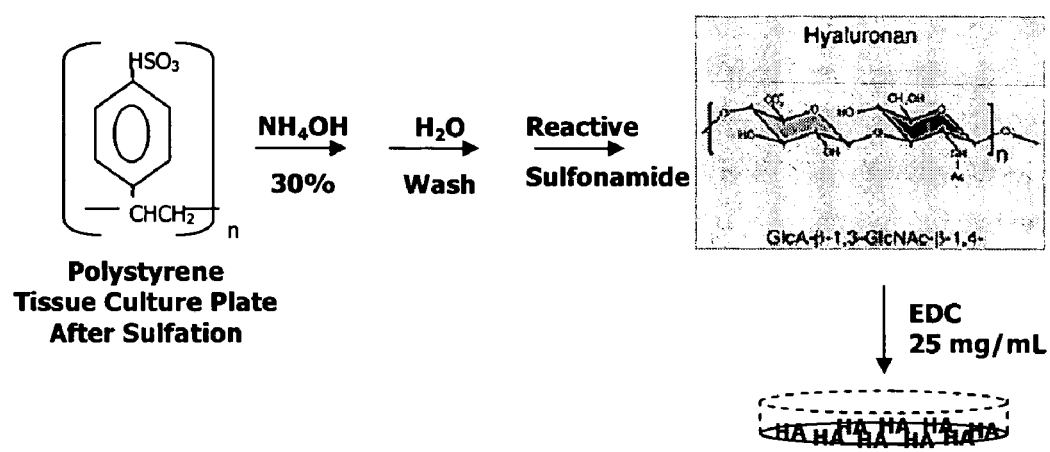

FIG. 2 is a representation of the chemical methods used to covalently attach HA to a polystyrene surface, originally described by Turley and Roth (Turely and Roth, 1979).

$HSO_3$, hydrogen sulfite ion; $NH_4OH$, liquid ammonia; $H_2O$, water; HA, hyaluronic acid; EDC, 3-(3-dimethylaminopropyl) carbodiimide hydrochloride.

Figure 3:
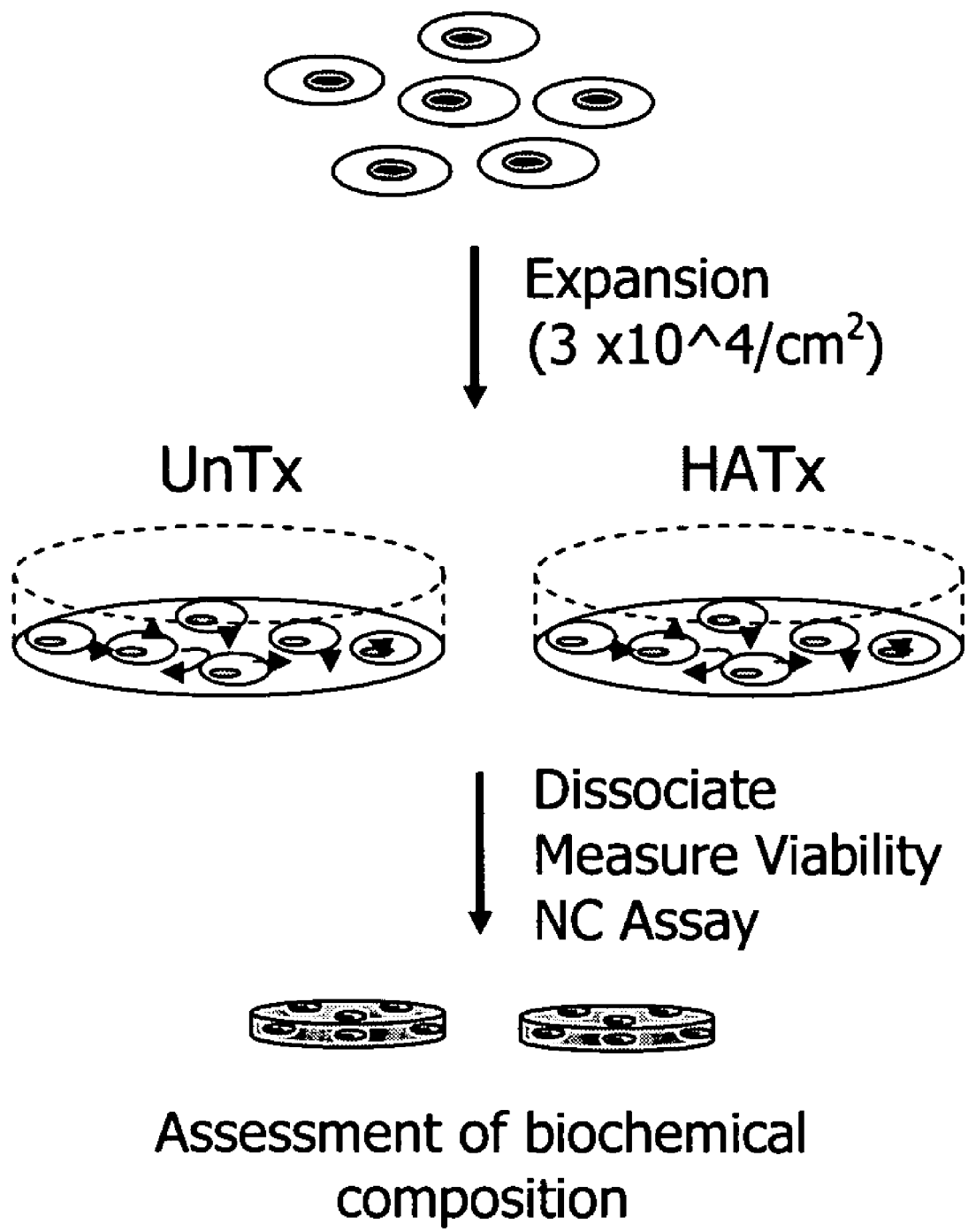

FIG. 3 is a graphic representation of the current method of cytokine-mediated chondrocyte expansion on a sodium hyaluronate substratum and subsequent growth of neocartilage.

UnTx, unmodified tissue culture plastic; HATx, HA modified tissue culture plastic; NC Assay, neocartilage functional assay.

Figure 4:
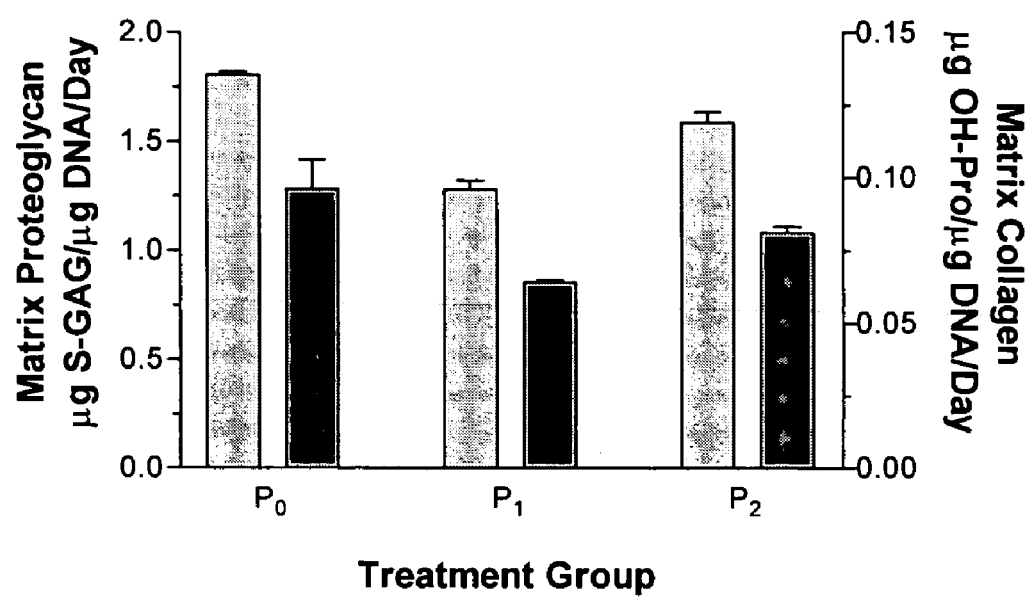

FIG. 4 shows the biochemical composition of NC grafts that were produced from chondrocytes that were expanded on HA modified polystyrene in defined serum-free medium containing basic fibroblast growth factor (bFGF), transforming growth factor beta (TGF$\beta$) and vitamin C as compared to freshly isolated chondrocytes. Chondrocytes were derived from young donor articular cartilage.

S-GAG, sulfated glycosaminoglycan; DNA, deoxyribose nucleic acid.

Figure 5A:
Figure 5B:
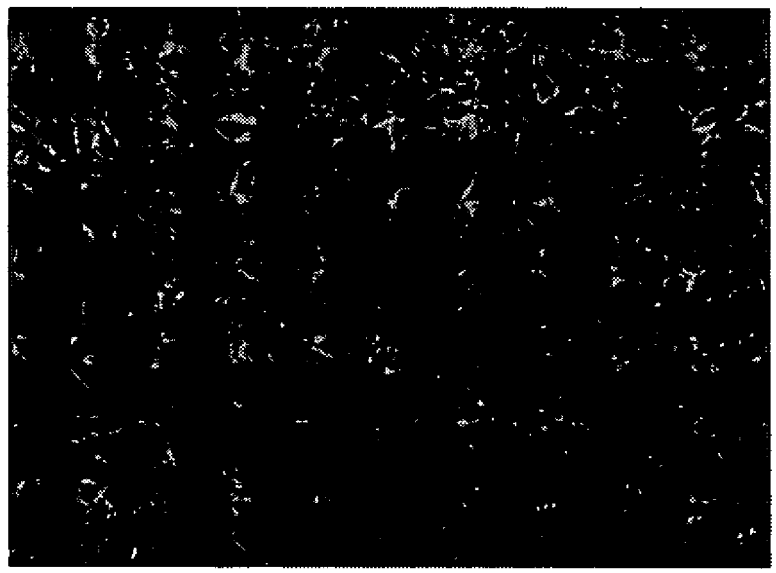

FIG. 5, in two parts, FIGS. 5A and 5B show the effect of covalently bound sodium hyaluronate on chondrocyte morphology. FIG. 5A shows the morphologic appearance of chondrocytes after 10 day expansion culture on HA modified polystyrene using a defined serum-free medium containing variant fibroblast growth factor 2 (vFGF2), TGF$\beta$ and vitamin C. FIG. 5B shows the morphologic appearance of the same chondrocytes grown on unmodified polystyrene using the conditions identified in A.

Figure 6:
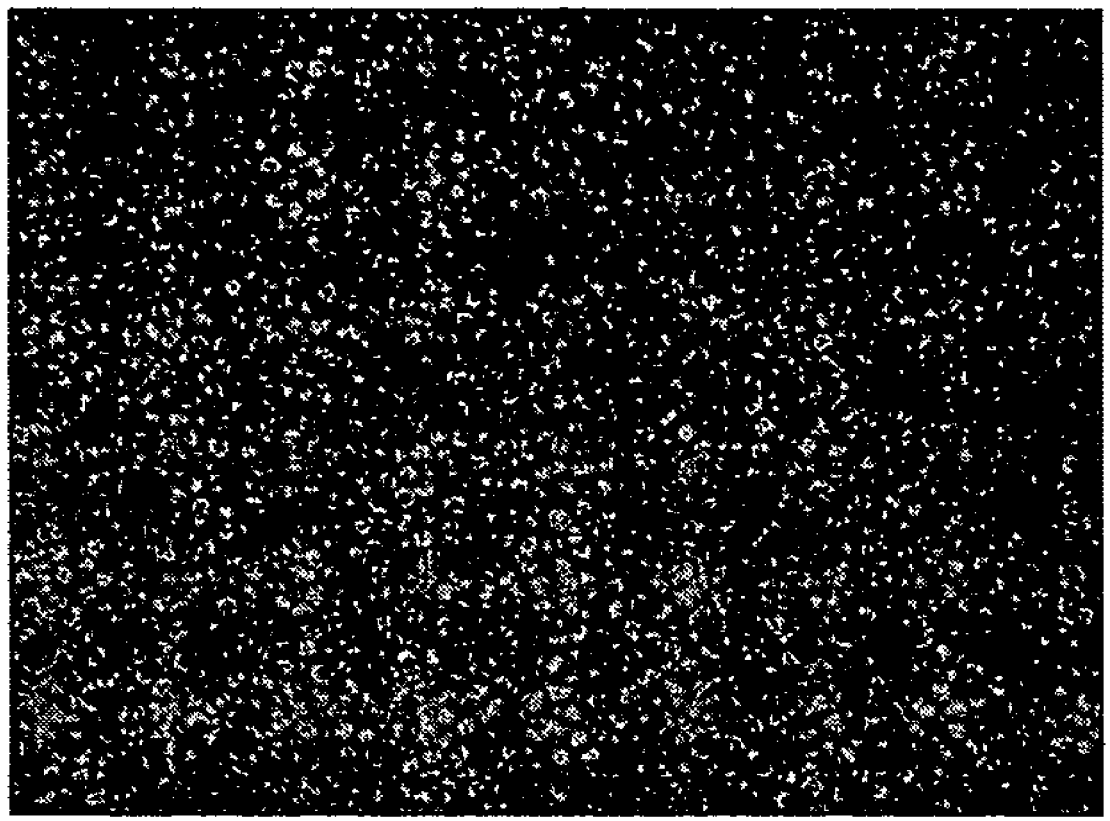

FIG. 6 is a photomicrograph of neocartilage produced from passage two chondrocytes ($P_2$) that were expanded on HA modified polystyrene in HL-1™ Complete Serum-free Medium containing variant fibroblast growth factor-2 (FGF- 2), transforming growth factor beta-2 (2 ng/mL) [ProChon Ltd.] and TGFβ-2 (10 ng/mL).

Figure 7:
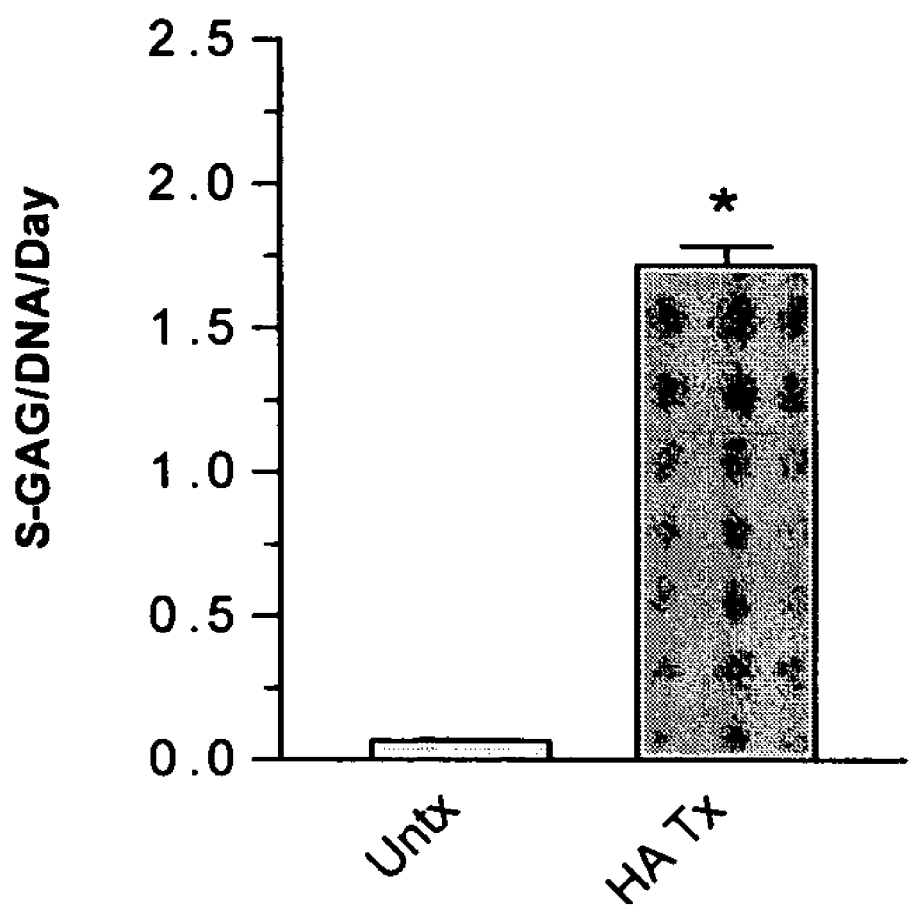

FIG. 7 is a graphic representation showing the biochemical composition of newly synthesized NC matrix from chondrocytes that were expanded on HA modified polystyrene versus control cells that were expanded on unmodified polystyrene.

S-GAG, sulfated glycosaminoglycan; DNA, deoxyribose nucleic acid; UnTx, unmodified tissue culture plastic; HATx, HA modified tissue culture plastic. *, denotes significance (P<0.05) relative to grafts that were produced with cells that were derived from expansion in the absence of HA-modified substrate.

Figures 8, 8A, 8B:
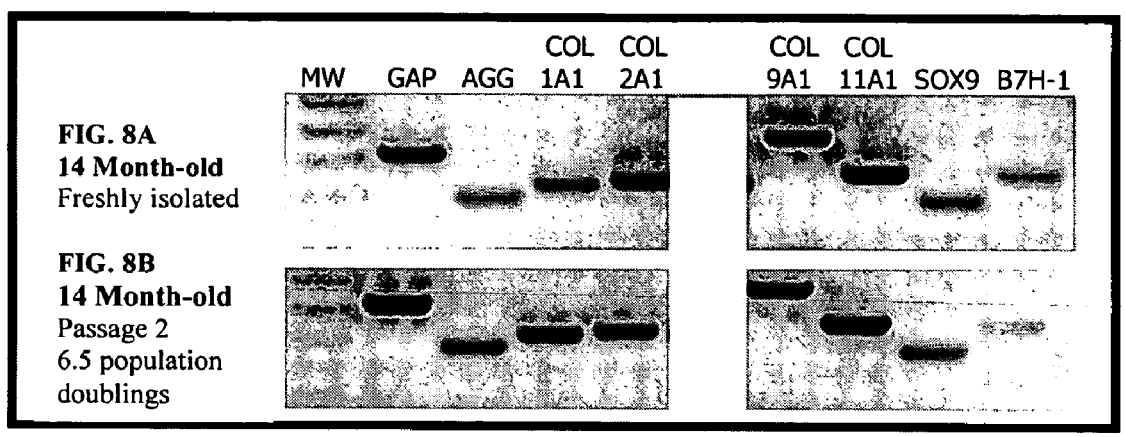

FIG. 8, in two parts, FIGS. 8A and 8B, represent gene expression profile analyses obtained for freshly dissociated unpassaged cells ($P_0$) and passage two cells ($P_2$) chondrocytes harvested from a 14 month-old donor. Semi quantitative gene expression analysis was performed using the reverse transcriptase-polymerase chain reaction (RT-PCR).

MW, molecular weight markers; GAP, glyceraldehydes-3-phosphate dehydrogenase; AGG, aggrecan core protein; COL 1A1, collagen type 1; COL 2A1, collagen type IIA; COL 9A1, collagen type IX; COL 11A1, collagen type XI; SOX9, cartilage specific transcription factor.

Figure 9:
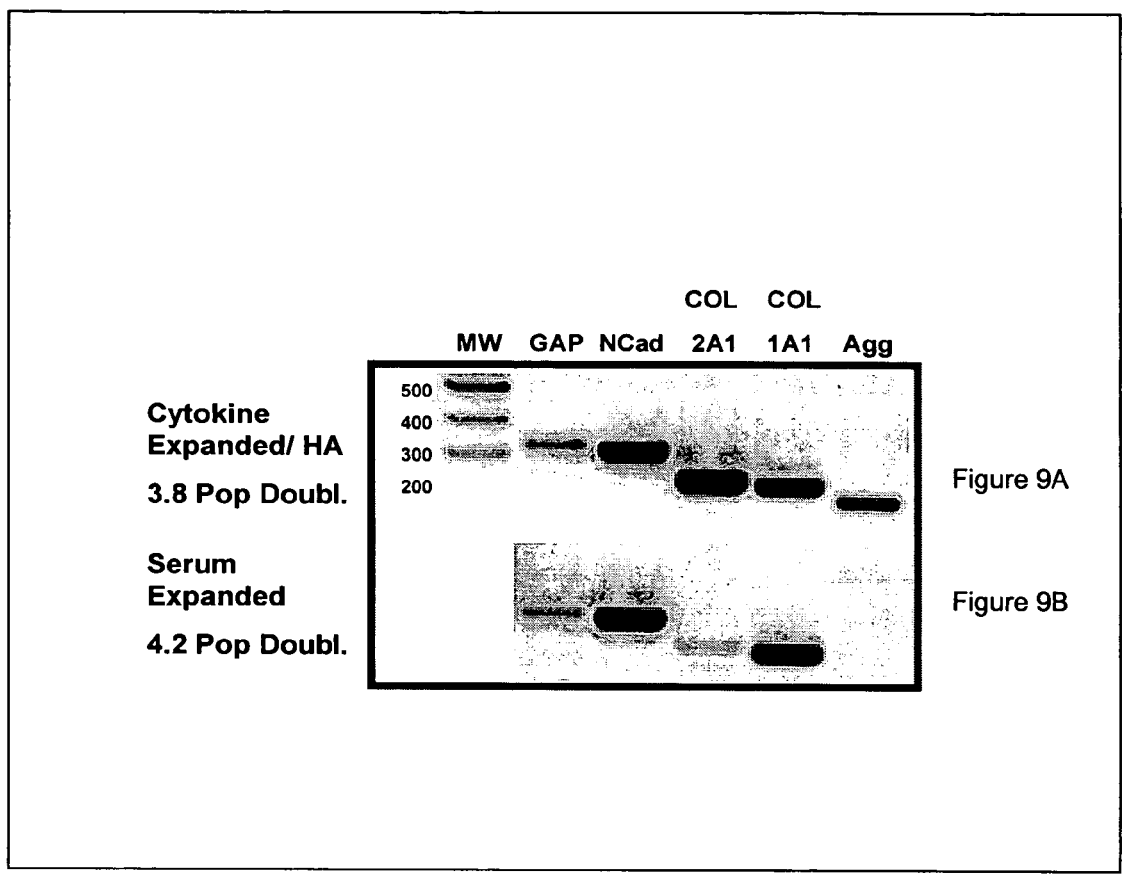

FIG. 9, in two parts, FIGS. 9A and 9B represent gene expression profile analyses obtained for articular chondrocytes derived from young donor cartilage that were expanded using methods of the described invention (Panel A) through 3.8 population doublings or in HL-1 Complete Serum-free Medium containing 10% serum and ascorbate (50 µg/mL) (Panel B) through 4.2 population doublings.

MW, molecular weight markers; GAP, glyceraldehydes-3-phosphate dehydrogenase; NCAD, N-cadherin; COL 2A1, collagen type 2; COL 1A1, collagen type IA; Agg, aggrecan core protein.

Figure 10:
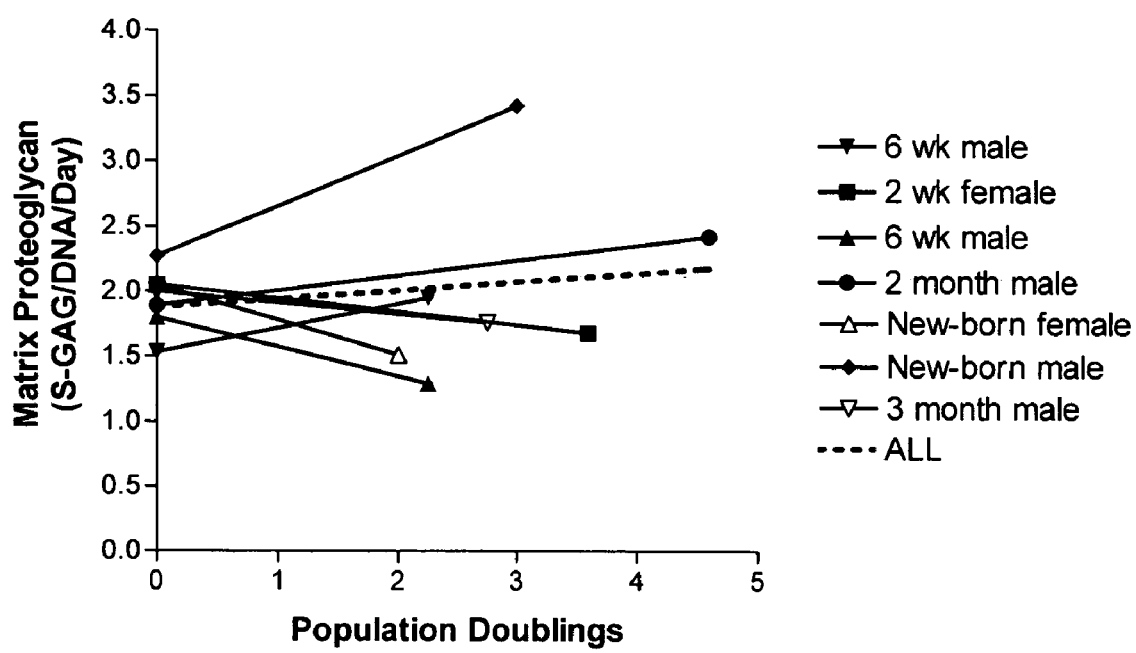

FIG. 10 is a graphic representation showing the reproducibility of large-scale chondrocyte expansion on HA-modified polystyrene using cells derived from different donor cartilage.

S-GAG, sulfated glycosaminoglycan; DNA, deoxyribose nucleic acid.

Figure 11:
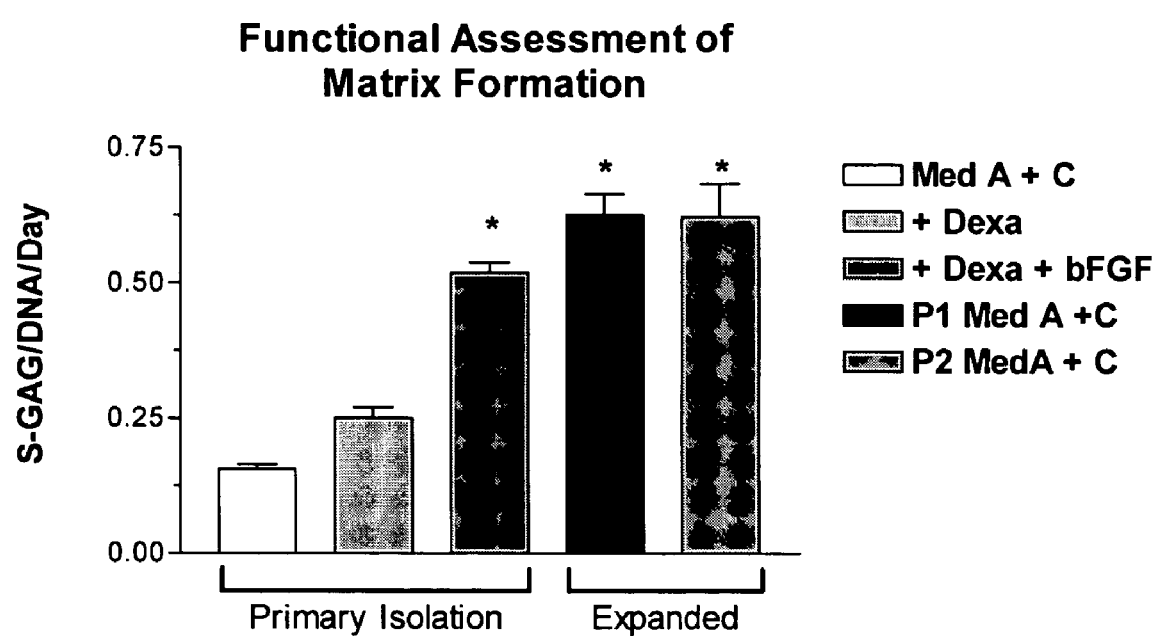

FIG. 11 is a graphic representation showing the biochemical composition of NC grafts that were produced from adult chondrocytes that were expanded on HA modified polystyrene through two passages in defined serum-free medium containing bFGF, TGF beta and vitamin C (cumulative increase of 5.8 population doublings). Chondrocytes were isolated from a 47 year-old male displaying Grade 1 osteoarthritis. Differentiation medium (Medium A) either contained dexamethasone ($10-8M$) or a combination of dexamethasone and bFGF (10 ng/mL) as indicated to further induce proteoglycan synthesis.

S-GAG, sulfated glycosaminoglycan; DNA, deoxyribose nucleic acid; dexa, dexamethasone 21-phosphate; bFGF, recombinant human fibroblast basic growth factor-2.

*, denotes significance (P<0.05) relative to the primary cells maintained in Media A containing vitamin C alone.

DETAILED DESCRIPTION OF THE PREFERRED EMBODIMENTS

Abbreviations and Definitions

The term "chondrocytes" refers to cartilage-specific cells that give rise to normal cartilage tissue growth in vivo; these cells synthesize and deposit the supportive matrix (composed principally of collagen and proteoglycan) of cartilage.

The term "phenotype" refers to the observable characteristics at any level—physical, morphologic, biochemical or molecular—of a cell or tissue.

The term "neocartilage" refers to cartilage grown ex vivo and characterized by one or more of the following attributes: containing membrane phospholipids enriched in Mead acid but substantially depleted of linoleic or arachidonic acid, being substantially free of endothelial, bone and synovial cells, having a sulfated glycosaminoglycan (S-GAG) content of at least 40 µg/µg of DNA; being substantially free of types I, III and X collagen; containing a matrix substantially free of biglycan; having multiple layers of cells randomly arranged, rather than separated, into distinct zones of chondrocyte maturation; being enriched in high molecular weight aggrecan, or being characterized by having multiple layers of cells surrounded by a substantially continuous insoluble glycosaminoglycan and collagen-enriched hyaline extracellular matrix.

The term "hyaluronate substrate" refers to a substrate containing a hyaluronate mixture that is in large part comprised of a natural or synthetic, highly purified hyaluronate, such as sodium hyaluronate purified either from rooster combs or from bacterial fermentation. Hyaluronic acid is a polysaccharide composed of repeating disaccharide units of N-acetylglucosamine and glucuronic acid. Commercial HA is commonly its sodium salt form.

The term "cytokine" refers to a vast array of relatively low molecular weight, pharmacologically active proteins that are secreted by one cell for the purpose of altering either its own function(s) (autocrine effect) or those of adjacent cells (paracrine effect). Individual cytokines can have multiple biological activities. Different cytokines can also have redundant activity.

The term "FGF" indicates the fibroblast growth factor family of related proteins, which currently numbers 22 members (in humans, FGF-1-14 and FGF-16-23). "FGF-2" refers to the basic form of fibroblast growth factor (FGF). FGFs generally have a high affinity for heparan sulfate proteoglycans; interactions between FGF and heparin appear necessary for activation of each the FGF receptors (Ornitz and Itoh 2001). There are four FGFRs (FGFR1-4), each having many splice variants. An "active form" of an FGF polypeptide is a polypeptide that has significant (greater than 70%) homology to at least a portion of a conserved region of any FGF polypeptide and possesses the same activity as at least one of its homologues. The degree of activity can be greater or less than at least one of the homologues. In most cases, an internal core region containing approximately 28 highly conserved and six identical amino-acid residues can be identified, ten of which habitually interact with FGFRs (Ornitz, 2000 and Plotnikov et al., 2000).

The term "FGF-like activity" refers to an activity of a molecule, such as a polypeptide, that acts on at least one cell type in a similar manner as the cognate FGF molecule in at least one aspect. For example, a molecule having FGF-like activity can be substituted for FGF during the expansion of chondrocytes in the methods of the invention.

The term "TGF-β" indicates the transforming growth factor family of related proteins. TGF-β proteins are recognizable by C-terminus polypeptide homology and their signaling via the Similar to Mothers Against Decapentaplegic (SMAD) proteins after binding TGF-β receptors. Examples include TGF-β1-3, bone morphogenenic proteins (BMPs), etc. An "active form" of a TGF-β polypeptide is a polypeptide displaying significant (greater than 70%) homology to at least a portion of a conserved region of a TGF-β polypeptide and possesses the same activity as at least one of its homologues. The degree of activity can be greater or less than at least one of the homologues.

The term "TGF-β-like activity" refers to an activity of a molecule (such as a polypeptide) that acts on at least one cell type in a similar manner as a cognate TGF-β molecule. For example, a molecule that signals via the SMAD proteins, regardless if the molecule has bound a TGF-β receptor or not, has TGF-β-like activity. TGF-β molecules stimulate synthesis of collagens, fibronectin, proteoglycans, tenascin, thrombospondin, plasminogen activator inhibitor-1 and tissue inhibitor of metalloprotease-1 proteins. A molecule having TGF-β-like activity, such as recombinant lactoferrin, can be substituted for TGF-β during the expansion of chondrocytes in the methods of the invention.

The following embodiments are given as non-limiting examples of various ways to practice the invention.

In all embodiments, the underlying principle is to maintain native chondrocyte phenotype by growing dissociated chondrocytes or chondroprogenitor cells on a substrate that is modified by covalent attachment of sodium hyaluronate and which supports maintenance of chondrocyte morphology and phenotype. The cartilaginous tissue produced therefrom is both biocompatible and safe for use in medical applications. The modified substratum provides a microenvironment that more closely mimics that of native articular cartilage, resulting in retention of rounded cell shape and hyaline cartilage gene expression. Chondrocytes adhere to immobilized HA via a cell surface glycoprotein receptor for hyaluronan (CD44) and can utilize the HA substratum to assemble the large proteoglycan aggregates typically found in normal, healthy articular cartilage.

High molecular weight HA (>400,000 MW) can be used as a substratum for in vitro expansion culture to increases total cell yield, while preventing loss of differentiated cell function. The growth of chondrocytes at low density on an HA modified substratum in chemically defined media significantly increases chondrocyte cell number. Moreover, chondrocytes expanded in this manner retain their native chondrogenic differentiation potential to produce neocartilage tissue, and these cells or the neocartilage produced therefrom can be used for clinical application. Therefore, this method serves to address the challenges identified in earlier cell-based approaches to articular cartilage repair.

One embodiment of the invention provides a method of producing chondrocytes by altering the surface chemistry of the tissue culture plastic by covalently attaching sodium hyaluronate to the plastic. Chondrocytes cultured on the modified plastic remain rounded and loosely attached during the expansion process. In time, the chondrocytes are observed to undergo condensation, forming tissue aggregates. This unique method of expanding chondrocytes allows the cells to retain their functional activity after expansion. The invention also provides for kits for the expansion of chondrocytes.

In yet another embodiment of the invention, a novel method for serially expanding chondrocytes in vitro on a substrate is provided. The method includes the steps of:

isolating chondrocytes; modifying a tissue culture surface via covalent attachment of hyaluronate acid; growing the chondrocytes on a modified substrate in a serum-free growth medium containing cytokines; and using the expanded chondrocytes to produce hyaline-like cartilage tissue or a population of cells that is useful for transplantation.

In a preferred method, chondrocytes are isolated from cartilage derived from immature donors, including neonatal, infant, or pre-adolescent donors for subsequent plating, e.g., on a polystyrene substrate to which sodium hyaluronate is covalently attached.

Chondrocytes can be avian or mammalian chondrocytes, preferably human chondrocytes. Chondrocytes can be derived from transgenic animals that have been genetically engineered to prevent immune-mediated xenograft rejection (Sandrin et al., 1995; Sandrin et al., 1996 and Osman et al., 1997). Cartilage can be obtained from any tissue containing hyaline, elastic or fibro-cartilage.

In contrast to other methods of expanding chondrocytes known in the art, such as seeding cells on three dimensional scaffolds or substrates that prevent cell spreading, further exogenous material beyond sodium hyaluronate is not required to produce differentiated chondrocytes during expansion. The method of the present invention provides for seeding chondrocytes in direct contact with an appropriate tissue culture surface, most preferably unmodified tissue-culture plastic, such as virgin polystyrene. Although scaffold material is unnecessary, it can be used, for example in the case of polystyrene microcarrier beads.

In a preferred embodiment, a cell culture is produced by isolating immature chondrocytes, e.g., neonatal, infant or pre-adolescent, from donor articular cartilage and plating the dissociated cells onto a tissue culture substrate that is first modified via covalent attachment of sodium hyaluronate.

Chondrocytes can be isolated by methods known in the art such as by sequential enzymatic digestion techniques (Adkisson et al., 2001).

The isolated chondrocytes can then be seeded directly on a tissue culture vessel in a basal medium comprising an effective amount of serum such as Dulbecco's modified Eagle's medium (DMEM) to allow adherence of the chondrocytes directly to the culture vessel and to promote mitogenesis. However, because serum has been observed to encourage the cells to de-differentiate, any serum-containing media is exchanged with a defined medium.

In a preferred embodiment of the invention, isolated chondrocytes are expanded on an HA-modified substrate.

Suitable substrates are any tissue culture plastics, such as virgin polystyrene, polycarbonate, polytetra-filters of fluoromethane or mixed cellulose esters (such as those inserts available from Millipore; Billerica, Md.) that can be modified to covalently attach hyaluronic acid. Other tissue culture substrates can also be used, such as inserts or surfaces coated with basement molecules (e.g., such as isolated from Engelbreth-Holm-Swarm tumors), or interstitial matrix, such as collagen types I, II, III, IV, V or VI. Other suitable substrata include those coated with extracts of *Mytilus edulis* (marine mussel, e.g., Cell-Tak™ Tissue Adhesive, BD Biosciences, San Jose, Calif.); cell-adhesive plasma proteins, such as vitronectin or fibronectin, and other synthetic cell-adhesive molecules, such as poly-L-lysine or poly-D-lysine. The only requirement for a suitable substrate is that it be amendable to modification with hyaluronic acid or N-acetylglucosamine, the natural building block to HA biosynthesis. Preferably, hyaluronic acid or N-acetylglucosamine is covalently attached, although a covalent linkage is not necessary in most cases, except for direct attachment to polystyrene substrata.

The covalent modification of the culture vessel with HA provides a substrate that no longer is soluble in aqueous media and therefore maintains native chondrocyte phenotype during cytokine-mediated expansion of chondrocytes in serum-free medium. Hyaluronic acid recapitulates a cartilage microenvironment, whereas unmodified tissue culture plastic (polystyrene) does not. However, any other molecules that promote aggrecan assembly can be used, for example recombinant link protein.

Cross-linkers (Pierce, Rockford, Ill. "Cross-linkers"; product literature 2004).

Cross-linking two or more molecules is to covalently join them. Cross-linkers, cross-linking reagents, etc., have portions that react with specific functional groups, such as primary amines, sulfhydryls, carboxyls, etc. Most commonly used cross-linkers come in two forms: homobifunctional and heterobifunctional, although cross-linking reagents can have more than two reactive groups (e.g., trifunctional cross-linkers). Homobifunctional linkers have two identical reactive groups, whereas heterobifunctional cross-linkers have two different reactive groups. Homobifunctional cross-linkers are used in "single-stage" cross-linking. To take advantage of heterobifunctional cross-linkers, "sequential-stage" cross-linking procedures are used. Most commonly used cross-linkers have chemically reactive groups; however, cross-linkers with photoreactive groups can be used. An advantage of photoreactive groups is that they can form conjugates that otherwise cannot be formed using chemically reactive groups, although the efficiency of photoreactive groups can be low, most often 10%, sometimes up to 70%.

Common heterobifunctional cross-linkers include those that have amine-reactive succinimidyl ester at one end, and a sulfhydrylreactive group at the other. Another example is the carbodiimides, which are "zero-length" cross-linkers and effect direct coupling between carboxylates and primary amines.

The selection of a cross-linker is based on the target functional groups of the molecules to be cross-linked and the compatibility of the reaction to the application. The following characteristics are also considered: chemical specificity, spacer arm length, reagent solubility (and in the case of cells, membrane permeability), whether a homo- or hetero-bifunctional agent is appropriate or desired, chemically reactive or photoreactive groups, desirability of cleavable links after cross-linking, and whether the reagent can be conjugated to a label (e.g., a radiolabel). Over 300 cross-linkers are currently available; one of skill in the art recognizes that multiple approaches can be used to chemically cross-link HA to various substrates without significantly altering the ability of the HA to interact with cells, particularly in the case of developing reagents with spacer arms of increased length to enable the HA to be freely accessible in three-dimensional space.

The most important question, perhaps, is what functional groups are available for coupling. For example, if only lysine residues or N-terminal amino acids are available, a logical choice is NHS-ester homobifunctional cross-linkers. If one molecule has lysine residues and the other sulfhydryls, a maleimide NHS-ester cross-linker is appropriate. If only lysine residues are available on both molecules, modification to introduce sulfhydryls via the lysine residues on one molecule would allow for sequential coupling. If both molecules have free sulfhydryls, a homobifunctional sulfhydryl reactive cross-linker is appropriate. If carboxyl groups and amines are available, carbodiimide works well. Furthermore, if there are no readily reactive groups, a photoactivatible cross-linker can be used. If lysine residues are important for the functionality of the molecule, then a cross-linker that affects coupling through sulthydryls, carboxyls, or is nonspecific can be used. TABLE I lists some classes of reactive cross-linker groups and their functional group targets.

TABLE I

Reactive cross-linker groups and their functional group targets

| Reactive group (classes) | Functional group (classes) | Reactive group (classes) | Functional group (classes) |
|---|---|---|---|
| aryl azide | non-selective (or primary amine) | Maleimide | sulfhydryl |
| carbodiimide | amine/carboxyl | NHS-ester[1] | amine |
| hydrazide | oxidized carbohydrate | PFP-ester[2] | amine |
| hydroxymethyl phosphine | amine | Psoralen | thymine (photoreactive intercaltor) |
| imidoester | Amine | pyridyl disulfide | sulfhydryl |
| isocyanate | non-aqueous hydroxyl | vinyl sulfone | sulfhydryl, amine, hydroxyl |

[1]NHS, aminosuccinimidyl
[2]PFP, pentafluorophenyl

Spacer arm lengths can play an important role in the success of cross-linking, and usually requires empirical determination. Usually, a short spacer arm (4-8 A) is first used and then the success of cross-linking is assessed. If linking is poor, then cross-linkers with longer spacer arms can be explored. In some instances, a cleavable cross-linking agent is desirable; for example, if one would want to release a culture of chondrocytes intact with the HA substrate. TABLE II identifies an expanded list of applicable double-agent cross-linkers. TABLE III identifies an expanded list of applicable single-agent cross-linkers.

TABLE II

Double-agents cross-linkers

| Agent | Reactive toward (X) Amines | Sulf-hydryls | Carbo-hydrates | Photo-reactive | Carboxyls | Hydroxyl |
|---|---|---|---|---|---|---|
| p-Azidobenzoyl Hydrazide (ABH) | | | X | X | | |
| 3-[(2-Aminoethyl)dithio]propionic acid · HCl (AEDP) | X | | | | X | |
| N-[α-Maleimidoacetoxy]succinimide ester (AMAS) | X | X | | | | |
| N-5-Azido-2-nitrobenzoyloxysuccinimide (ANB-NOS) | X | | | X | | |
| N-[4-(p-Azidosalicylamido)butyl]-3'-(2'-pyridyldithio)propionamide (APDP) | | X | | X | | |
| p-Azidophenyl glyoxal monohydrate (APG) | | | | X | | |
| 4-[p-Azidosalicylamido butylamine (ASBA) | | | | X | X | |
| Bis-[β-(4-Azidosalicylamido)ethyl]disulfide (BASED) | | | | X | | |
| 1,4-Bis-maleimidobutane (BMB) | | X | | | | |
| Bis-Maleimidoethane (BMOE) | | X | | | | |
| N-β-Maleimidopropionic acid (BMPA) | X | X | | | | |
| N-[β-Maleimidopropionic acid]hydrazide · TFA (BMPH) | | X | X | | | |
| N-[β-Maleimidopropyloxy]succinimide ester (BMPS) | X | X | | | | |
| 1,8-Bis-Maleimidotriethyleneglycol (BM[PEO]$_3$) | | X | | | | |

TABLE II-continued

| Double-agents cross-linkers | | |
|---|---|---|
| 1,11-bis-Maleimidotriethyleneglycol (BM[PEO]₄) | | X |
| Bis[2-Succinimidyloxycarbonyloxy)-ethylsulfone (BSOCOES) | X | |
| Bis[Sulfosuccinimidyl]suberate (BS3) | X | |
| 1,5-Difluora-2,4-dinitrobenzene (DFDNB) | X | |
| Dimethyl adipimidate · 2 HCl (DMA) | X | |
| Dimethyl pimelimidate · 2 HCl (DMP) | X | |
| Dimethyl suberimidate · 2 HCl (DMS) | X | |
| 1,4-Di[3'-(2'-pyridyldithio)-propionamido]butane (DPDPB) | | X |
| Disuccinimidyl glutarate (DSG) | X | |
| Dithiobis[succinimidyl propionate] (DSP) | X | |
| Disuccinimidyl suberate (DSS) | X | |
| Disuccinimidyl tartrate (DST) | X | |
| Dimethyl 3,3'-dithiobispropionimidate · 2 HCl (DTBP) | X | |
| Dithio-bis-maleimidoethane (DTME) | | X |
| 3,3'-Dithiobis[sulfosuccinimidyl propionate] (DTSSP) | X | |
| 1-Ethyl-3-[3-dimethylaminopropyl]carbodiimide Hydrochloride (EDC) | X | X |
| Ethylene glycol bis[succinimidylsuccinate] (EGS) | X | |
| N-ε-Maleimidocaproic acid) (EMCA) | X | X |
| N-[ε-Maleimidocaproic acid]hydrazide (EMCH) | | X X |
| N-[ε-Maleimidocaproyloxy]succinimide ester (EMCS) | X | X |
| N-[γ-Maleimidobutyryloxy]succinimide ester (GMBS) | X | X |
| 1,6-Hexane-bis-vinylsulfone (HBVS) | | X |
| N-κ-Maleimidoundecanoic acid (KMUA) | | X X |
| N-[κ-Maleimidoundecanoic acid]hydrazide (KMUH) | | X X |
| Succinimidyl-4[N-maleimidomethyl]-cyclohexane-1-carboxy-[6-amidocaproate] (LC-SMCC) | X | X |
| Succinimidyl 6-[3-(2-pyridyldithio)-proionamido]hexanoate (LC-SPDP) | X | X |
| m-Maleimidobenzoyl-N-hydroxysuccinimide ester (MBS) | X | X |

| Agent | Cleavable by (○) | | | | Iodinatable |
|---|---|---|---|---|---|
| | Thiols | Base | Periodate | Hydroxylamine | |
| p-Azidobenzoyl Hydrazide (ABH) | | | | | N |
| 3-[(2-Aminoethyl)dithio]propionic acid · HCl (AEDP) | ○ | | | | N |
| N-[α-Maleimidoacetoxy]succinimide ester (AMAS) | | | | | N |
| N-5-Azido-2-nitrobenzoyloxysuccinimide (ANB-NOS) | | | | | N |
| N-[4-(p-Azidosalicylamido)butyl]-3'-(2'-pyridyldithio)propionamide (APDP) | ○ | | | | Y |
| p-Azidophenyl glyoxal monohydrate (APG) | | | | | N |
| 4-[p-Azidosalicylamido butylamine (ASBA) | | | | | Y |
| Bis-[β-(4-Azidosalicylamido)ethyl]disulfide (BASED) | ○ | | | | Y |
| 1,4-Bis-maleimidobutane (BMB) | | | | | N |
| Bis-Maleimidoethane (BMOE) | | | | | N |
| N-β-Maleimidopropionic acid (BMPA) | | | | | N |
| N-[β-Maleimidopropionic acid]hydrazide · TFA (BMPH) | | | | | N |
| N-[β-Maleimidopropyloxy]succinimide ester (BMPS) | | | | | N |
| 1,8-Bis-Maleimidotriethyleneglycol (BM[PEO]₃) | | | | | N |
| 1,11-bis-Maleimidotriethyleneglycol (BM[PEO]₄) | | | | | N |
| Bis[2-Succinimidyloxycarbonyloxy)-ethylsulfone (BSOCOES) | | ○ | | | N |
| Bis[Sulfosuccinimidyl]suberate (BS3) | | | | | N |
| 1,5-Difluora-2,4-dinitrobenzene (DFDNB) | | | | | N |
| Dimethyl adipimidate · 2 HCl (DMA) | | | | | N |
| Dimethyl pimelimidate · 2 HCl (DMP) | | | | | N |
| Dimethyl suberimidate · 2 HCl (DMS) | | | | | N |
| 1,4-Di[3'-(2'-pyridyldithio)-propionamido]butane (DPDPB) | ○ | | | | N |
| Disuccinimidyl glutarate (DSG) | | | | | N |
| Dithiobis[succinimidyl propionate] (DSP) | ○ | | | | N |
| Disuccinimidyl suberate (DSS) | | | | | N |
| Disuccinimidyl tartrate (DST) | | | ○ | | N |
| Dimethyl 3,3'-dithiobispropionimidate · 2 HCl (DTBP) | ○ | | | | N |
| Dithio-bis-maleimidoethane (DTME) | ○ | | | | N |
| 3,3'-Dithiobis[sulfosuccinimidyl propionate] (DTSSP) | ○ | | | | N |
| 1-Ethyl-3-[3-dimethylaminopropyl]carbodiimide Hydrochloride (EDC) | | | | | N |
| Ethylene glycol bis[succinimidylsuccinate] (EGS) | | | | ○ | N |
| N-ε-Maleimidocaproic acid) (EMCA) | | | | | N |
| N-[ε-Maleimidocaproic acid]hydrazide (EMCH) | | | | | N |
| N-[ε-Maleimidocaproyloxy]succinimide ester (EMCS) | | | | | N |
| N-[γ-Maleimidobutyryloxy]succinimide ester (GMBS) | | | | | N |
| 1,6-Hexane-bis-vinylsulfone (HBVS) | | | | | N |
| N-κ-Maleimidoundecanoic acid (KMUA) | | | | | N |
| N-[κ-Maleimidoundecanoic acid]hydrazide (KMUH) | | | | | N |
| Succinimidyl-4[N-maleimidomethyl]-cyclohexane-1-carboxy-[6-amidocaproate] (LC-SMCC) | | | | | N |
| Succinimidyl 6-[3-(2-pyridyldithio)-proionamido]hexanoate (LC-SPDP) | ○ | | | | N |
| m-Maleimidobenzoyl-N-hydroxysuccinimide ester (MBS) | | | | | N |

TABLE III

Single-agents cross-linkers

| Agent | Reactive toward (X) | | | | | |
|---|---|---|---|---|---|---|
| | Amines | Sulf-hydryls | Carbo-hydrates | Photo-reactive | Carboxyl | Hydroxyl |
| 4-[N-Maleimidomethyl]cyclohexane-1-carboxylhydrazide · ½dioxane($M_2C_2H$) | | X | X | | | |
| 3-Maleimidophenyl boronic acid(MPBH) | | X | X | | | |
| Methyl N-succinimidyl adipate(MSA) | X | | | | | |
| N-Hydroxysuccinimidyl-4-azidosalicylic acid(NHS-ASA) | X | | | X | | |
| 3[2-Pyridyldithio]propionl hydrazide(PDPH) | | X | X | | | |
| N-[p-Maleimidophenyl]isocyanate(PMPI) | | X | | | | X |
| N-Succinimidyl[4-azidophenyl]-1,3'-dithiopropionate(SADP) | X | | | X | | |
| Sulfosuccinimidyl 2-[7-axido-4-methylcoumarin-3-acetamido]ethyl-1,3'-dithiopropionate(SAED) | X | | | X | | |
| Sulfosuccinimidyl 2-[m-azido-o-nitro-benzamido]ethyl-1,3'-dithiopropionate(SAND) | X | | | X | | |
| N-Succinimidyl 6-[4'-azido-2'-nitro-phenylamino]hexanoateSANPAH | X | | | X | | |
| Sulfosuccinimidyl-2-[p-azido-salicylamido]ethyl-1,3'-dithiopropionate(SASD) | X | | | X | | |
| N-Succinimidyl S-acetylthioacetate(SATA) | X | X | | | | |
| N-Succinimidyl S-acetylthiopropionate(SATP) | X | X | | | | |
| Succinimidyl 3-[bromoacetamido]propionate(SBAP) | X | X | | | | |
| Sulfosuccinimidyl-[perfluoroazido-benzamido]-ethyl-1,3'-dithiopropionate(SFAD) | X | | | X | | |
| N-Succinimidyl iodoacetate(SIA) | X | X | | | | |
| N-Succinimidyl[4-iodoacetyl]aminobenzoate(SIAB) | X | X | | | | |
| Succinimidyl 4-[N-maleimidomethyl]-cyclohexane-1-carboxylate](SMCC) | X | X | | | | |
| Succinimidyl 4-[p-maleimidophenyl]butyrate(SMPB) | X | X | | | | |
| Succinimidyl-6-[(β-maleimidopropionamido)hexanoate](SMPH) | X | X | | | | |
| 4-Succinimidyloxy carbonyl-methyl-α[2-pyridyldithio]toluene(SMPT) | X | X | | | | |
| N-Succinimidyl 3-[2-pyridyldithio]propionate(SPDP) | X | X | | | | |
| Bis[2-(Sulfosuccinimido oxycarbonyloxy)-ethyl]sulfone(Sulfo-BSOCOES) | X | | | | | |
| Disulfosuccinimidyl tartrate(Sulfo-DST) | X | | | | | |
| Ethylene glycol bis[sulfosuccinimidylsuccinate](Sulfo-EGS) | X | | | | | |
| N-[ε-Maleimidocaproyloxy]sulfosuccinimide ester(Sulfo-EMCS) | X | X | | | | |
| N-[γ-Maleimidobutyryloxy]sulfo-succinimide ester(Sulfo-GMBS) | X | X | | | | |
| N-Hydroxysulfosuccinimidyl-4-azidobenzoate(Sulfo-HSAB) | X | | | X | | |
| N-[κ-Maleimidoundecanoyloxy]-sulfosuccinimide ester(Sulfo-KMUS) | X | X | | | | |
| Sulfosuccinimidyl 6-[3'-(2-pyridyldithio)-propionamido]hexanoateSulfo-LC-SPDP | X | X | | | | |
| m-Maleimidobenzoyl-N-hydroxysulfo-succinimide ester(Sulfo-MBS) | X | X | | | | |
| Sulfosuccinimidyl[4-azidosalicylamido]-hexanoate(Sulfo-NHS-LC-ASA) | X | | | X | | |
| Sulfosuccinimidyl[4-azidophenyldithio]-propionate(Sulfo-SADP) | X | | | X | | |
| Sulfosuccinimidyl 6-[4'-azido-2'-nitro-phenylamino]hexanoate(Sulfo-SANPAH) | X | | | X | | |
| Sulfosuccinimidyl[4-iodoacetyl]aminobenzoate(Sulfo-SIAB) | X | X | | | | |
| Sulfosuccinimidyl 4-[N-maleimidomethyl]-cyclohexane-1-carboxylate(Sulfo-SMCC) | X | X | | | | |
| Sulfosuccinimidyl 4-[p-maleimidophenyl]-butyrate(Sulfo-SMPB) | X | X | | | | |
| Sulfosuccinimidyl-6-[α-methyl-α-(2-pyridyldithio)toluamido]hexanoate(Sulfo-LC-SMPT) | X | X | | | | |
| Sulfosuccinimidyl[2-6-(biotinamido)-2-(p-azidobenamido)-hexanoamido]ethyl-1,3'-dithioproionate(Sulfo-SBED) | X | | | X | | |
| N-Succinimidyl-[4-vinylsulfony]benzoate(SVSB) | X | X | | | | |
| N-[ε-Trifluoroacetylcaproyloxy]succinimide ester(TFCS) | X | | | | X | |
| β-[Tris(hydroxymethyl)phosphino]-propionic acid (betaine)(THPP) | X | | | | | |
| Tris-[2-maleimidoethyl]amine(TMEA) | | X | | | | |
| Tris-succinimidyl aminotriacetate(TSAT) | X | | | | | |

| Agent | Cleavable by (O) | | | | | Latent functional group |
|---|---|---|---|---|---|---|
| | Thiol | Base | Periodate | Hydroxyl-amine | Iodina-table | |
| 4-[N-Maleimidomethyl]cyclohexane-1-carboxylhydrazide · ½dioxane($M_2C_2H$) | | | | | N | |
| 3-Maleimidophenyl boronic acid(MPBH) | | | | | N | |
| Methyl N-succinimidyl adipate(MSA) | | | | | N | CO—OH |
| N-Hydroxysuccinimidyl-4-azidosalicylic acid(NHS-ASA) | | | | | Y | |
| 3[2-Pyridyldithio]propionl hydrazide(PDPH) | O | | | | N | |
| N-[p-Maleimidophenyl]isocyanate(PMPI) | | | | | N | |
| N-Succinimidyl[4-azidophenyl]-1,3'-dithiopropionate(SADP) | O | | | | N | |
| Sulfosuccinimidyl 2-[7-axido-4-methylcoumarin-3-acetamido]ethyl-1,3'-dithiopropionate(SAED) | O | | | | N | |
| Sulfosuccinimidyl 2-[m-azido-o-nitro-benzamido]ethyl-1,3'-dithiopropionate(SAND) | O | | | | N | |
| N-Succinimidyl 6-[4'-azido-2'-nitro-phenylamino]hexanoateSANPAH | | | | | N | |

TABLE III-continued

Single-agents cross-linkers

| Name | C1 | C2 | C3 | C4 | C5 | Group |
|---|---|---|---|---|---|---|
| Sulfosuccinimidyl-2-[p-azido-salicylamido]ethyl-1,3'-dithiopropionate(SASD) | ○ | | | | Y | |
| N-Succinimidyl S-acetylthioacetate(SATA) | | | | | N | —SH |
| N-Succinimidyl S-acetylthiopropionate(SATP) | | | | | N | —SH |
| Succinimidyl 3-[bromoacetamido]propionate(SBAP) | | | | | N | |
| Sulfosuccinimidyl-[perfluoroazido-benzamido]-ethyl-1,3'-dithiopropionate(SFAD) | ○ | | | | N | |
| N-Succinimidyl iodoacetate(SIA) | | | | | N | |
| N-Succinimidyl[4-iodoacetyl]aminobenzoate(SIAB) | | | | | N | |
| Succinimidyl 4-[N-maleimidomethyl]-cyclohexane-1-carboxylate](SMCC) | | | | | N | |
| Succinimidyl 4-[p-maleimidophenyl]butyrate(SMPB) | | | | | N | |
| Succinimidyl-6-[(β-maleimidopropionamido)hexanoate](SMPH) | | | | | N | |
| 4-Succinimidyloxy carbonyl-methyl-α[2-pyridyldithio]toluene(SMPT) | ○ | | | | N | |
| N-Succinimidyl 3-[2-pyridyldithio]propionate(SPDP) | ○ | | | | N | |
| Bis[2-(Sulfosuccinimido oxycarbonyloxy)-ethyl]sulfone(Sulfo-BSOCOES) | | ○ | | | N | |
| Disulfosuccinimidyl tartrate(Sulfo-DST) | | | ○ | | N | |
| Ethylene glycol bis[sulfosuccinimidylsuccinate](Sulfo-EGS) | | | | ○ | N | |
| N-[ε-Maleimidocaproyloxy]sulfosuccinimide ester(Sulfo-EMCS) | | | | | N | |
| N-[γ-Maleimidobutyryloxy]sulfo-succinimide ester(Sulfo-GMBS) | | | | | N | |
| N-Hydroxysulfosuccinimidyl-4-azidobenzoate(Sulfo-HSAB) | | | | | N | |
| N-[κ-Maleimidoundecanoyloxy]-sulfosuccinimide ester(Sulfo-KMUS) | | | | | N | |
| Sulfosuccinimidyl 6-[3'-(2-pyridyldithio)-propionamido]hexanoateSulfo-LC-SPDP | ○ | | | | N | |
| m-Maleimidobenzoyl-N-hydroxysulfo-succinimide ester(Sulfo-MBS) | | | | | N | |
| Sulfosuccinimidyl[4-azidosalicylamido]-hexanoate(Sulfo-NHS-LC-ASA) | | | | | Y | |
| Sulfosuccinimidyl[4-azidophenyldithio]-propionate(Sulfo-SADP) | ○ | | | | N | |
| Sulfosuccinimidyl 6-[4'-azido-2'-nitro-phenylamino]hexanoate(Sulfo-SANPAH) | | | | | N | |
| Sulfosuccinimidyl[4-iodoacetyl]aminobenzoate(Sulfo-SIAB) | | | | | N | |
| Sulfosuccinimidyl 4-[N-maleimidomethyl]-cyclohexane-1-carboxylate(Sulfo-SMCC) | | | | | N | |
| Sulfosuccinimidyl 4-[p-maleimidophenyl]-butyrate(Sulfo-SMPB) | | | | | N | |
| Sulfosuccinimidyl-6-[α-methyl-α-(2-pyridyldithio)toluamido]hexanoate(Sulfo-LC-SMPT) | ○ | | | | N | |
| Sulfosuccinimidyl[2-6-(biotinamido)-2-(p-azidobenamido)-hexanoamido]ethyl-1,3'-dithioproionate(Sulfo-SBED) | ○ | | | | N | |
| N-Succinimidyl-[4-vinylsulfony]benzoate(SVSB) | | | | | N | |
| N-[ε-Trifluoroacetylcaproyloxy]succinimide ester(TFCS) | | | | | | $NH_2$ |
| β-[Tris(hydroxymethyl)phosphino]-propionic acid (betaine)(THPP) | | | | | N | |
| Tris-[2-maleimidoethyl]amine(TMEA) | | | | | N | |
| Tris-succinimidyl aminotriacetate(TSAT) | | | | | N | |

Sodium periodate can be used to create reactive aldehyde groups for crosslinking of glycosaminoglycans to a variety of structures containing available primary amines through the formation of a stable Schiff base. Glycosaminoglycans such as chondroitin sulfate, dextran and sodium hyaluronate have been modified using such procedures. Most recently, Liu et al., 2003 described the preparation of hyaluronate-polyaldehydes to form a tissue engineering scaffold useful for bone repair (Healos™) (Liu et al., 2003).

In this way, activated hyaluronate-polyaldehyde is prepared by oxidizing sodium hyaluronate with sodium periodate, followed by extensive dialysis. The density of reactive aldehydes (formyl groups) on the hyaluronate polymer can be controlled by altering the reaction time, and can be monitored quantitatively using a modification of the bicinchoninic acid method (Hermanson GT Bioconjugate Techniques. San Diego, Academic Press, Inc, 1996, p 622). Consequently, an alternative method for cross linking sodium hyaluronate to polystyrene surfaces involves Schiff base formation between the sulfonamide created in the first step with the reactive aldehydes of periodate-oxidized HA. The lyophilized HA-polyaldehyde is stable at 4° C. (dark storage). An aqueous solution of the polyaldehyde is added to the modified polystyrene surface and allowed to react either at room temperature or at 37° C., depending on the extent of cross-linking desired. Unreacted material is then removed by aspiration, and the plates are washed extensively in distilled water and culture medium prior to seeding with cells.

In the isolations of cells from tissues for the methods of the invention, care should be taken during enzymatic digestion to optimize total cell yield and viability. Traditionally, chondrocytes have been isolated from cartilage tissue by sequential enzymatic digestion, using a nonspecific protease followed by a mixture of collagenase and hyaluronidase. Unfortunately, most preparations of proteolytic enzymes used for research purposes contain significant levels of endotoxin, as well as a variety of undesirable proteolytic activities that can damage cell membrane proteins, leading to apoptotic cell death.

"Blendzyme™" preparations were developed by Roche Diagnostics Corporation (Indianapolis, Ind.) to address the increasing demand for proteases with characterized enzymatic activity and purity. From a regulatory perspective, these enzymes are preferred materials for use in the manufacturing of tissue engineered medical products. Blendzyme™ 2 contains a combination of collagenase and neutral protease activity that works well for harvesting primary chondrocytes from articular cartilage. Reduced levels of the same enzyme are preferred when chondrocytes are released from a culture substrate.

Blendzymes are blends of purified collagenases I and II and a neutral protease. The collagenases are purified from the fermentation of *Clostridium histolyticum*. Currently four formulations are available. Blendzyme™ 1 contains the neutral protease dispase, which is purified from *Bacillus polymyxa* fermentation. Blendzymes™ 2, 3 and 4 contain the neutral protease thermolysin, purified from *Bacillus thermoproteolyticus* fermentation. The methods for purifying and blending these components for Blendyme™ preparation have been described in U.S. Pat. Nos. 5,753,485 and 5,830,741. The use of Blendzyme™ mixes can be optimized using the criteria presented in TABLE IV.

TABLE IV

Optimizing Blendzyme ™ Use

| Observation 1 | Observation 2 | Possible cause | Recommendation |
|---|---|---|---|
| Low cell viability | Dissociation very rapid | Enzyme concentration too high Blendzyme number too high | Reduce enzyme concentration by 50%. Move down one Blendzyme level, keep initial concentration. |
| | Dissociation very slow | Enzyme concentration too low Blendzyme number too low | Increase enzyme concentration by 50%. Move up one Blendzyme level, keep initial concentration. |
| Impaired cell function | Cell viability >80%, cell yield is reasonable | Enzyme concentration too high Blendzyme number too high | Reduce enzyme concentration by 25%. Move down one Blendzyme level, keep initial concentration. |
| Low cell yield | Cell viability >80% | Enzyme concentration too low Blendzyme number too low | Increase enzyme concentration by 25–50%. Move up one Blendzyme level, keep initial concentration. |
| | Cell viability <80% | Enzyme concentration too high Blendzyme number too high Mechanical (shear) force is excessive | Reduce enzyme concentration by 50%. Move down one Blendzyme level, keep initial concentration. Reduce shear force in all aspects of dissociation. Treat tissue gently. |
| Released cells clump in gelatinous stringy form | Cell yield and viability are acceptable | DNA release, subsequent to cell lysis, is causing clumping | More prevalent in some tissues. If cell viability is acceptable, add DNase to dissociation mixture |
| | Cell yield or viability are reduced | Mechanical (shear) force is excessive | Reduce shear force in all aspects of dissociation. Treat tissue gently. |

While Blendzymes are preferred, any method that safely releases the cells can be used, including those that use chelating agents, with and without enzymes. Ethylenediaminetetraacetic acid (EDTA) and ethylene-bis (oxyethylenenitrilo) tetraacetic acid (EGTA) are two such common reagents that can be used singly, or in combination.

In a preferred embodiment of the invention, chondrocytes are isolated from immature donors such as neonatal, infants, or pre-adolescents, and expanded on a substrate surface material, such as polystyrene, that is covalently modified via covalent attachment of sodium hyaluronate. The expanded cells are grown in a chemically defined serum-free growth medium to produce cartilage for cartilage repair.

Chondrogenic Progenitor Stem Cells.

Other cells that are suitable for the methods of the invention include those isolated from placenta (Kogler et al., 2004), bone marrow mesenchymal stromal cells (Mackay et al., 1998; Kavalkovick et al., 2002), adipose stromal cells (Huang et al., 2004), synovium (DeBari et al., 2004) and periosteum (DeBari et al., 2001).

The serum-free growth medium can also comprise vitamin C, ascorbate, exogenous autocrine growth factors or conditioned growth media as described below. When culturing cells according to the methods of the invention, the presence of vitamin C (ascorbic acid) is preferred. Vitamin C can be supplied in any active form, as a free acid or as a salt. Examples include calcium ascorbate, magnesium ascorbate, sodium ascorbate and L-ascorbic acid 2-phosphate or an esterified derivative thereof. The concentration to be used can be determined empirically, depending on the source of the cells, but usually, concentrations range from $5.6 \times 10^{-4}$ g/L to $5.0 \times 10^{-2}$ g/L when supplied as sodium ascorbate. Likewise, the serum free growth medium can comprise dexamethasone, or a salt derivative thereof. Dexamethasone enhances SOX 9 expression and presumably will increase the capacity for cartilage matrix production in the expanded cells (Sekiya et al., 2001; Malpeli et al., 2004).

The cell culture can be grown under suitable culture conditions such as growing the cell culture at 37 degrees C. in a humidified atmosphere with the addition of 2-10% $CO_2$, preferably 5%.

Doubling Time.

Depending on various factors, including initial plating density, quality of the growth media, genetic factors inherent in the cells, temperature, the quality of HA and its application to the substrate etc., the doubling time for a particular group of cells may vary. The doubling time observed for chondrocytes that are maintained as described in the present invention is generally 3 to 4 days, when plated at a density of $3 \times 10^4/cm^2$. When the length of time for expansion culture is increased to day 14 and 17, as many as 4-6 chondrocyte population doublings can be achieved. In contrast, the same cells grown in serum-supplemented media are limited by contact inhibition and produce no greater than two population doublings. A preferred defined medium used in the present invention is HL-1, a proprietary formulation containing insulin-transferrin-selenium-complex as its only source of protein (HL-1™ of Cambrex, Walkersville, Md.). The serum-free growth medium containing cytokines is either completely or partially replaced every three to four days after the initial seed.

Optimal media selection depends on the cell type; that media used to culture the cells usually represents a preferred option. Examples of suitable culture media include Iscove's Modified Dulbecco's Medium (IMDM), Dulbecco's Modified Eagle's Medium (DMEM), Minimal Essential Medium Eagle (MEM), Basal Medium Eagle (BME), Click's Medium, L-15 Medium Leibovitz, McCoy's 5A Medium, Glasgow Minimum Essential Medium (GMEM), NCTC 109 Medium, Williams' Medium E, RPMI-1640, Medium 199 and Ham's F12.

A medium specifically developed for a particular cell type/line other than chondrocytes may not be useful in the practice of this invention, particularly if it contains epidermal growth factor which is reported to induce chondrogenic dedifferentiation (Yoon et al., 2002).

In some cases, a protein can be added to support the cells, such as various albumins, including bovine serum albumin. If desired, the media can be further supplemented with reagents that limit acidosis of the cultures, such as buffer addition to the medium (such as N,N-bis(2-hydroxyethyl)-2-aminoethanesulfonic acid (BES), bis(2-hydroxyethyl) amino-tris(hydroxymethyl)methane (BIS-Tris), N-(2-hydroxyethyl)piperazine-N'3-propanesulfonic acid (EPPS or HEPPS), glyclclycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris(hydroxymethyl)-aminom-ethane (Tris), etc.). Frequent medium changes and changes in the supplied $CO_2$ (often approximately 5%) concentration can also be used to control acidosis.

The sources of various materials used in the specific laboratory examples are as follows:

Materials—Dulbecco's Modified Eagle's medium (DMEM) with added L-glutamine, sodium pyruvate, and glucose (either 1.0 g/liter [LG] or 4.5 g/liter [HG]), fetal bovine serum (FBS) and antibiotic (100 times) (penicillin G, sodium (10,000 units) and streptomycin sulfate (25 mg/ml in normal saline) were obtained from Life Technologies, Inc. (Grand Island, N.Y.).

Pronase-E (Type XIV, from *Streptomyces griseus*), hyaluronidase (type VIII, bovine testes), N-tris [hydroxymethyl] methyl-2-aminoethanesulfonic acid (TES), and MILLEX-GS syringe sterilization filters were obtained from Sigma Chemical Company (St. Louis, Mo.).

Collagenase (CLS 4) was purchased from Worthington Biochemicals (Freehold, N.J.). Tissue-culture dishes (35 mm dia., 100 mm dia, 12 and 24 well clusters) and bottle top sterilization filter units (type CA) were obtained from Costar Corporation (Cambridge, Mass.).

Bovine serum albumin (fraction V, fatty acid-free) was from Calbiochem (San Diego, Calif.). HL-1 Complete Serum-free Medium was obtained from Cambrex.

In another preferred embodiment, chondrocyte expansion in vivo is for cartilage repair. In this embodiment, cartilage is removed from a non-damaged cartilage area around a damage site and digested with collagenase. The resulting chondrocytes are expanded on the modified substrate of the invention, then injected or implanted into the cartilage defect site. Similarly, marrow stromal fibroblasts can be isolated from a normal area adjacent a bone defect, expanded ex vivo as described and administered at the site of a bone defect.

The expansion of chondrocytes of the invention (U.S. Pat. No. 6,617,161) containing platelet derived growth factor (PDGF), epidermal growth factor (EGF), fibroblast growth factor (FGF), and bone morphogenetic proteins results in the loss of two main cartilage-specific phenotypic markers, type II collagen and proteoglycan aggrecan, which are critical components for cartilage assembly and repair. Discontinued expression of these molecules indicates that the cells have undergone phenotypic dedifferentiation. Yoon et al., 2000 recently demonstrated that EGF promotes loss of native chondrocyte phenotype.

Chondrocytes cultured on unmodified polystyrene develop a fibroblastic appearance, displaying an elongated cell shape relative to their native rounded morphology. The characterization of phenotypic markers in the expanded chondrocyte population is necessary to establish the potential functional properties of the manipulated cells. Food and Drug Administration (FDA)/Center for Biologics Evaluation and Research (CBER) requires that protocols relating to ex vivo expansion of articular chondrocytes for repair of joint surfaces prove that the expanded cell populations are very similar to the native chondrocytes. This can be assessed by measuring mRNA expression levels of aggrecan core protein and type II collagen at the end of the expansion protocol by any appropriate method, including molecular methods (e.g., Northern blotting, RT-PCR) and biochemical methods (e.g., immunoprecipitation; affinity chromatography) or immunocytochemical methods (e.g., immunofluorescence-activated cell sorting (FACS)). Those protocols that detect the target proteins are preferred.

Any bioactive molecule that improves the proliferation, differentiation potential or quality of the resulting regenerated tissue can be used according to the present invention.

Expansion of cells on the HA-modified substrate also improves the efficiency of transfection of nucleic acids into the cells. Typically, nucleic acid transfer is carried out during monolayer expansion, and cells in active mitosis are more amenable to DNA transduction. Therefore, applications where tissue engineering techniques are combined with gene therapy can be utilized in accordance with the teachings of the present invention. For example, cells can be transfected with a vector that confers resistance to a variety of biological and chemical compounds, such as antibiotics, cytokines and inflammatory agents, or with a vector that result in the overexpressesion and synthesis of a particular growth factor or matrix component.

Implantation

Dissociated cells isolated from the expansion process of the present invention are typically grown without scaffold support to create a three-dimensional tissue for cartilage repair (U.S. Pat. No. 6,235,316). However, cells expanded via this method can be implanted in combination with suitable biodegradable, polymeric matrix or hydrogel to form new cartilage tissue. There are two forms of matrices which can be used: a polymeric hydrogel formed of a material, such as fibrin or alginate, having cells suspended therein, and a fibrous matrix having an interstitial spacing between about 40 and 200 microns. Preferred polymeric matrices are those that degrade in about one to two months after implantation; such as polylactic acid-glycolic acid copolymers (U.S. Pat. No. 5,716,404). The matrices can be seeded prior to implantation or implanted, allowed to vascularize, then seeded with cells. (Cima et al., 1991; Vacanti et al., 1988; and Vacanti et al., 1988).

Other materials, such as bioactive molecules that enhance vascularization of the implanted tissue and/or inhibit fibrotic tissue ingrowth can be implanted with the matrix to enhance development of more normal tissue.

EXAMPLE 1

Loss of Chondrocyte Phenotype by Serial Expansion in Serum Containing Media

Chondrocytes, regardless of tissue origin, rapidly lose the ability to synthesize cartilage specific macromolecules with serial expansion in vitro (Homicz et al., 2002; Mandl et al., 2002). Although juvenile chondrocytes are thought to better retain the ability to synthesize matrix macromolecules than adult articular chondrocytes, the following experiment was performed to determine the effect of serial expansion on chondrocyte matrix synthesis using chondrocytes derived from immature articular cartilage. A variety of media containing serum were evaluated to demonstrate the deleterious effects of serum on chondrocyte differentiation potential.

Sixteen (16) different donor cell populations were isolated from cadaveric articular cartilage ranging in age from newborn to three years. Four different basal medium formulations containing the indicated amount of fetal bovine serum were used: 10% DMEM/LG, 10% DMEM/LG to DMEM/LG, 10% DMEM/HG and 5% HL-1 to HL-1. T-75 flasks containing $3 \times 10^4$ cells/cm$^2$ were seeded and cultured for twenty-one days with complete exchange of growth medium occurring twice per week. Chondrocytes were released from the cultures by enzymatic dissociation, and total cell number and viability were estimated with fluorescent detection using a Guava Personal Cell Analysis system (Guava Technologies, Inc, Hayward, Calif.). Dissociated cells ($1 \times 10^6$ viable cells) were subsequently seeded in 48 well plates using HL-1 complete serum-free medium to produce neocartilage as described by Adkisson et al, 2001. Cultures were harvested for biochemical composition analysis on day 45 of culture.

Figure 1:
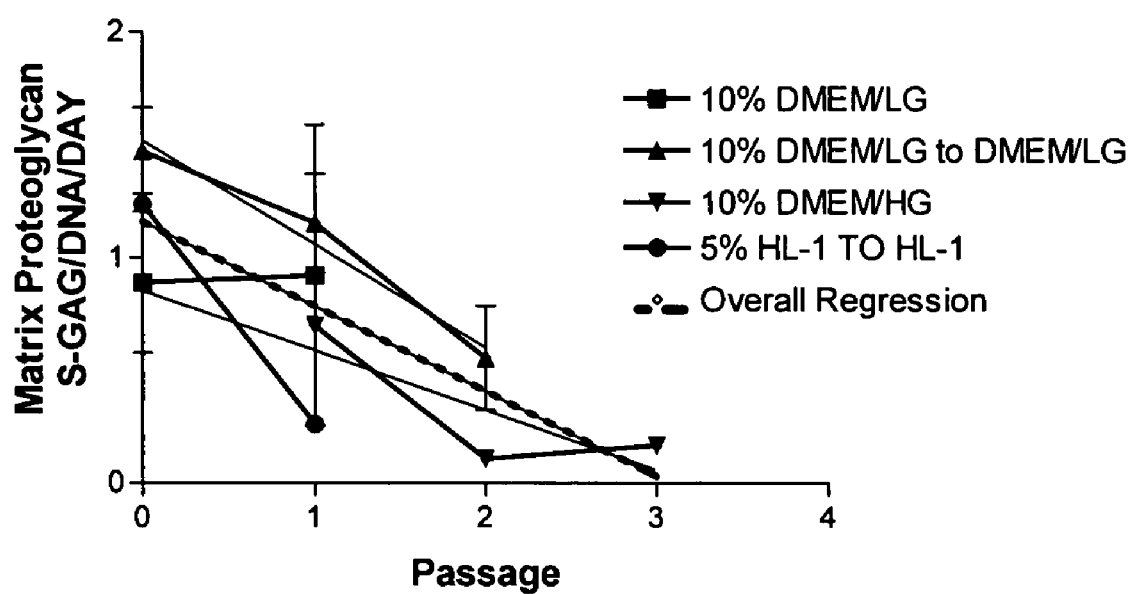
FIG. 1 is a graphic representation showing loss of chondrocyte differentiation potential as a function of passage number in serum containing medium. Young donor articular chondrocytes were expanded to passage three in serum containing medium using four different basal medium formulations.

FIG. 1 is a graphic representation showing loss of chondrocyte differentiation potential as a function of serial expansion in serum-containing medium. Two of the groups were expanded through two passages to a maximum of 2.8 population doublings (nearly an eight-fold increase in total cell number). A marked loss in the ability of juvenile articular chondrocytes to produce cartilageneous proteoglycan was observed. An overall regression line was plotted from the data which demonstrated a greater than 70% reduction in chondrocyte matrix synthesis after nearly three population doublings, relative to non-expanded chondrocytes derived from the same individuals.

Similar to what has been reported to occur in adult articular chondrocytes, these data illustrate that chondrocytes derived from young tissue donors rapidly lose the ability to assemble matrix proteoglycans after serial expansion in monolayer culture when maintained in various growth media containing fetal bovine serum ranging from 5-10% (v/v). Thus it appears that serum-derived factors, in contrast to donor age, determines in large part the extent to which chondrocytes dedifferentiate in vitro during monolayer culture, resulting in a significant loss in neocartilage matrix formation potential.

EXAMPLE 2

Method for Covalent Immobilization of Sodium Hyaluronate on Polystyrene Surfaces To improve the efficiency with which chondrocytes can be expanded in vitro without loss of native chondrocyte phenotype, juvenile chondrocytes were grown on a modified substratum prepared via covalent attachment of high molecular weight sodium hylauronate to polystyrene. It was hypothesized that immobilized sodium hyaluronate, in contrast to unmodified tissue culture plastic, would provide a microenvironment that could more closely mimic that of native articular cartilage. The following method for chemical modification of polystyrene with sodium hylauronate is a modification of that originally described by Turely and Roth (Turely and Roth, 1979).

In FIG. 2, the virgin polystyrene plates were treated with sulfuric acid at 37° C. for two hours. After removing the sulfuric acid and extensive washing of the plates in deionized distilled water, the reactive sulfonamide was created by adding aqueous ammonium hydroxide (24 hours at room temp.). The base was removed, and the plates again were washed extensively with water. Finally, a solution of high molecular weight sodium hyaluronate (HyluMed, Medical Grade, Genzyme Advanced Biomaterials, Cambridge, Mass.; 5 mg/mL in water) was cross-linked to the reactive sulfonamide using 3-(3-dimethylaminopropyl) carbodiimide (EDC) hydrochloride (48 hours at 37° C.). This process is depicted in FIG. 2. Prior to initiating the expansion cultures, hyaluronate/EDC solution was removed by aspiration, and the tissue culture plates were washed extensively in deionized distilled water, followed by two washes in HL-1 Complete Serum-free Medium (Cambrex).

EXAMPLE 3

Chondrocyte Phenotype Retained by Serial Expansion on HA-coated Plastic in Serum-free Medium Chondrocytes derived from a six week-old subject were taken through two passages using plates that were modified by the method illustrated in Example 2. Differentiation potential of the expanded chondrocytes was assessed after enzymatic dissociation and estimation of total cell number and viability. A proprietary serum-free differentiation medium, developed at Isto Technologies, Inc, was used to stimulate chondrocyte differentiation. In contrast to other methods, such as that described by Martin et al. (U.S. Pat. No. 6,582,960), this medium contains neither TGFβ nor dexamethasone to enhance chondrogenic differentiation potential, and the only protein component in this formulation is recombinant human insulin (Serologicals Corporation, Milford, Mass.).

FIG. 3 shows a schematic representation of the process of cytokine-mediated chondrocyte expansion in which covalent attachment of sodium hyaluronate serves as a substratum for maintenance of chondrocyte phenotype during expansion. Primary chondrocytes are isolated, washed and resuspended at a final density of $3 \times 10^4$ cells/cm$^2$ in HL-1 Complete Serum-free Medium containing 100 ng/mL FGF-2 and 20/ng/mL TGFβ and vitamin C. Control and HA-treated plates were harvested after 14-17 days of expansion using Blendzyme 2 as described in Example 7. An aliquot of the dissociated cells was plated in differentiation medium to assess neocartilage formation potential, while the remaining cells underwent serial expansion. Neocartilage was harvested from differentiation cultures between day 28 and 45 for measurement of total proteoglycan, DNA and collagen content in the neocartilage matrix. These values were compared to those obtained for neocartilage prepared from non-expanded chondrocytes using the same methods. The total cumulative increase in chondrocyte number was 85-fold or 6.5 population doublings.

FIG. 4 illustrates the biochemical composition data that was collected on grafts produced from the freshly dissociated unpassaged cells ($P_0$) and passage two cells ($P_2$). Neocartilage grafts were initiated at a density of $1 \times 10^6$ cells/well in untreated 48-well plates using freshly dissociated cells and cells from each successive passage to $P_2$. The rates of glycosaminoglycan (S-GAG/DNA/Day) and collagen (hydroxyproline/DNA/Day) synthesis are plotted on the left-and right-hand axis, respectively. Data represent replicates of four to five±sd. Estimated population doublings for each expansion was 2.25 and 4.25 at passage one cells ($P_1$) and $P_2$, respectively, at day 14 and 17 of culture.

Young donor chondrocytes that were expanded on HA-modified polystyrene in defined serum-free medium containing FGF and TGFβ showed minimal loss of differentiation potential relative to the freshly isolated chondrocytes. As shown in FIG. 4, the proteoglycan content of $P_1$ and $P_2$ neocartilage is within 78-88% of that of the primary cultures, indicating that little change in the rate of extracellular matrix synthesis occurred as a result of the expansion conditions. In contrast to chondrocyte expansion in 10% fetal bovine serum (see data Example 1), these levels reflect a three- to four-fold increase in total matrix production over cells that were expanded in a variety of serum-containing media. In fact, neocartilage grafts produced from young donor chondrocytes that were expanded on HA-modified plastic in a chemically defined growth medium were found to make rigid tissue discs that were easily manipulated ex vivo with forceps.

In a separate experiment, growth of expanded chondrocytes (differentiation assay) on HA-modified plastic resulted in a 25% increase in total matrix production (both sulfated glycosaminoglycan and collagen), relative to growth on unmodified tissue culture plastic. These data suggest that immobilization of HA to the culture surface prior to chondrocyte differentiation directs neocartilage formation, resulting in greater production of cartilage extracellular matrix and supports the earlier work of Kujawa et al. (1986). In contrast to Kujawa et al., the present work illustrates that there is no dependents on size of HA polymer.

With the ultimate goal of establishing in vitro conditions for chondrocyte expansion that are efficient, reproducible and which result in maintenance of normal chondrocyte phenotype, this example illustrates that a plastic surface modified by covalent attachment of sodium hyaluronate limits chondrocyte spreading during expansion and retains the functional properties of the expanded chondrocytes.

EXAMPLE 4

Chondrocytes Expanded on Covalently Bound Sodium Hyaluronate Maintain Rounded Morphology and Native Function.

This example demonstrates that chondrocytes cultured on an HA-coated substratum in defined medium results in maintenance of native chondrocyte phenotype by retaining rounded cell shape and function.

Human $P_1$ chondrocytes, derived from a five year-old, having first been expanded on unmodified plastic in the presence of cytokine, were used in this pilot experiment to determine if immobilized HA could restore both rounded chondrocyte morphology and the functional properties of the cells after enzymatic dissociation. Thirty-five mm diameter polystyrene dishes were modified via covalent attachment of sodium HA as described. $2\times10^5$ chondrocytes were harvested from an expansion of primary cells and subsequently seeded onto HA-modified and unmodified polystyrene surfaces for further expansion in HL-1 Complete Serum-free Medium (Cambrex) containing 2 ng/mL TGFβ-2 and 10 ng/mL variant human FGF-2 (ProChon, Ltd., Rehovat, Israel) and vitamin C. Cultures were harvested on day 10 for enumeration and estimation of viability using Guava ViaCount reagents. Greater than 2.5 population doublings were achieved at day 10 of culture.

FIG. 5A illustrates that chondrocytes expanded in the presence of cytokines on HA-modified polystyrene form chondrocyte islands or aggregates in which the chondrocytes appear to maintain a rounded morphologic appearance. Formation of these cartilage aggregates is reminiscent of the condensation of mesenchymal tissue which normally occurs in vivo during skeletal development (Singley and Solursh, 1981). The relative opacity of the chondrocyte aggregates suggests that the chondrocytes continue to actively synthesize extracellular matrix components. Thus, chondrocytes grown on the HA modified surface formed clusters of cells that retained a rounded morphology, characteristics of the chondrocyte phenotype.

In contrast, the same cells expanded under identical conditions on unmodified plates exhibited a flattened, cobblestone appearance (FIG. 5B). In these cultures, chondrocyte expansion potential appeared to be limited by contact inhibition.

Chondrocytes from each of these groups were subsequently passaged by dissociation in collagenase and hyaluronidase and seeded ($1\times10^6$ per well) into 48-well culture dishes (unmodified) to measure the capacity to which the $P_2$ cells synthesize neocartilage matrix. Using chemically defined conditions to optimize matrix production (see example 3) in the absence of three-dimensional scaffolds or pellet culture, the chondrocytes were grown for 45 days, at which time they were harvested for biochemical composition analysis. FIG. 6 shows a photomicrograph of neocartilage obtained at Day 10 of culture, illustrating the rounded morphologic appearance of $P_2$ cells that were harvested from expansion culture on HA-modified polystyrene. Chondrocytes expanded by this method and placed in differentiation culture displayed a rounded morphologic appearance characteristic of freshly dissociated chondrocytes. FIG. 7 compares the biochemical composition of newly synthesized NC matrix obtained for chondrocytes that were expanded on HA modified plastic to that of the same cells that were expanded on unmodified polystyrene.

Substrate containing covalently bound HA appears to preserve native chondrocyte morphology (rounded phenotype) during neocartilage tissue formation, and more importantly, to restore chondrocyte extracellular matrix synthesis in expanded cells to a level that approached that of the primary culture population (approximately 1.75 to 2 μg S-GAG/μg DNA/Day).

EXAMPLE 5

Characterization of Chondrocyte Phenotype at The Molecular Level

Maintenance of native chondrocyte phenotype in cells that had been expanded on HA-modified polystyrene was confirmed at the molecular level by gene expression analysis. Chondrocytes harvested at each passage in scale-up experiments were used for RNA isolation, and the relative mRNA levels corresponding to a set of cartilage-specific extracellular matrix macromolecules and the cartilage transcription factor, SOX 9, were analyzed using semi-quantitative reverse transcriptase polymerase chain reaction (RT-PCR).

FIGS. 8A and 8B show representative gene expression profiles obtained for $P_0$ and $P_2$ chondrocytes that were harvested from the cells used in Example 4 above. Note that $P_2$ cells have gone through a total of 6.5 population doublings. No discernable difference was observed in the pattern of gene expression obtained from freshly dissociated chondrocytes (upper panel) and the same cells after 6.5 population doublings (lower panel). mRNA levels for SOX 9 and B7-H1 remained unchanged after serial expansion. B7-H1 is the putative negative regulator of alloreactivity that is thought to maintain the immune privilege status of chondrocytes in vitro and in vivo (Adkisson et al., unpublished observations).

Even though the P$_2$ cells have gone through 6.5 cumulative population doublings, a point at which prior studies have described significant changes in cartilage-specific gene expression (Dell'Accio et al., 2001), these cells maintained a pattern of gene expression that was substantially the same as P$_0$ cells. With little change in the level of SOX9 gene expression in the P$_2$ chondrocytes, it was expected that the expression of genes controlling collagen and aggrecan core protein synthesis would show little change in expression level. This hypothesis was confirmed by gene expression profile analysis of mRNA encoding for aggrecan core protein and collagen types II, IX and XI, as well as collagen type I, which is associated with fibro-cartilage formation. It is noteworthy that a significant loss in the level of aggrecan core protein and type II collagen gene expression was observed in the same population of chondrocytes that were serially expanded in HL-1 medium containing 10% FBS and vitamin C (FIG. 9A and FIG. 9B). As shown in Example 1, chondrocytes expanded in serum containing media also lose their functional capacity to synthesize and assemble neocartilage matrix.

This experiment showed that chondrocyte expansion on a hyaluronate-modified substratum represents a preferred microenvironment that results in maintenance of native phenotype as demonstrated by morphological analysis of chondrocyte cell shape and gene expression profiling. By contrast, chondrocytes that were expanded in serum containing medium showed marked changes in mRNA levels for aggrecan core protein and type II collagen, two macromolecules essential for cartilage formation and repair.

EXAMPLE 6

Large-scale Chondrocyte Expansion and Reproducibility

Chondrocytes from seven different donors were plated at a density of $3 \times 10^4$ cells/cm$^2$ in T-75 tissue culture flasks containing supplemented, defined media. Cultures were grown for 14-20 days, at which time the cells were enzymatically dissociated and counted. Passage one cells were subsequently used to generate neocartilage discs in 48 well plates that were harvested between day 21 and 28 of culture for biochemical analysis. Biochemical composition data are plotted as the rate of proteoglycan synthesis (tissue matrix) versus number of population doublings, after normalizing the data to DNA content and the number of days in culture (FIG. 10).

FIG. 10 illustrates that juvenile chondrocytes expanded under these defined serum-free conditions, resulted in insignificant loss of matrix proteoglycan production after expansion to a range of 3 to 5 population doublings in a single passage. Regression analysis demonstrates retention of chondrogenic differentiation potential after nearly 5 population doublings in a single passage. Although the limits of chondrocyte expansion using this method and the ability to retain chondrocyte function with further dissociation and serial passage are not entirely clear, there is the ability to produce 4.5 billion cells from a single donor, assuming an initial cell yield of 150 million cells. Therefore, the present expansion method has the potential to treat hundreds of patients with a cell-based tissue engineered neocartilage product and represents a significant scientific advancement in the field by outperforming current autologous approaches to cartilage repair. Autologous Chondrocyte Implantation provides cell-based therapy to a single subject.

EXAMPLE 7

Materials and Methods

Isolation of Chondrocytes

Unless otherwise indicated, chondrocytes were isolated from the indicated sources by sequential enzymatic digestion as described previously (U.S. Pat. No. 6,235,316). Briefly, minced articular cartilage was exposed to protease from *Streptomyces Griseus* at 37° C. for 20 min., followed by overnight digestion (16-18 hrs) in HL-1 medium (15 mL) containing 2000 units CLS4 collagenase (Worthington, Lakewood, N.J.) and 1200 units hyaluronidase Type VIII (Sigma), gentamicin (50 µg/mL) and ascorbic acid (50 µg/mL). The next morning, the chondrocyte suspension was gently titrated and pelleted at 500×g for 8 minutes in a clinical centrifuge.

The harvesting of chondrocytes from expansion culture utilized a reduced concentration of collagenase/hyaluronidase (60/50 units/mL), respectively. Protease from *Streptomyces Griseus* was not necessary for this isolation procedure. Viability and total cell number were estimated using a Guava Personal Cell Analysis System (Guava Technologies, Inc, Hayward, Calif.) and fluorescent detection prior to using the cells in subsequent expansion or differentiation culture. The experiments presented in Example 6 utilized Liberase Enzymes manufactured by Roche Diagnostics Corporation (Indianapolis, Ind.). The concentration of Blendzyme 2 used to isolate chondrocytes from young donor cartilage was established empirically at 6.38 Wunsch units per gram of tissue (5 mL volume). The neutral protease activity of this preparation is 1.4 units thermolysin per gram of tissue. For dissociation of expansion cultures, the final concentration of Blendzyme 2 was 0.2 Wunsch units per mL. Tissue digestion required 8-10 hrs to reach completion, whereas expansion culture digestion was complete at 3-4 hrs.

Cell Culture

Chondrocyte cultures were maintained at 37° C. in a humidified environment supplemented with 5% CO$_2$. Media, as indicated in the examples, included DMEM, both high (HG) and low glucose (LG) formulations, supplemented with 2 mM L-glutamine (Sigma) and 50 µg/mL gentamicin. HL-1 Complete Serum-free Medium was purchased from Cambrex Bio Science (Walkersville, Md.). HL-1 medium is a chemically defined complete serum-free medium containing less than 30 µg protein/ml. Components of HL-1 include a modified DMEM/F12 base, HEPES buffer, known amounts of insulin, transferrin, sodium selenite and proprietary levels of dihydrotestosterone, ethanolamine, a variety of saturated and unsaturated fatty acids and stabilizing proteins. It contains no bovine serum albumin or other undefined protein mixtures. HL-1 was formulated to support the serum-free growth of various hybridomas and certain other differentiated cells of lymphoid origin.

Chondrocyte expansion cultures were established in HL-1 medium containing gentamicin (50 µg/mL), ascorbic acid (50 µg/mL) and the indicated concentration of recombinant human TGF-β1 or TGF-β3 (10-20 ng/ml) and recombinant human FGF-2 (2-100 ng/ml). These cytokines were purchased from R&D Systems (Minneapolis, Minn.). A variant form of FGF-2, purchased from ProChon, Ltd (Rehovat, Israel), was used as described in Example 4.

In vitro production of neocartilage for biochemical and gene expression profile analyses was optimized using a proprietary formulation developed at Isto Technologies, Inc (Media A). This medium contained no additional protein source other than 1×insulin, transferrin, selenite mixture available from Sima (Cat No. I-3146) or recombinant human insulin alone (Serologicals Corporation). Cells were plated at 1×10$^6$ per well in 48-well Tissue Culture plates manufactured by Corning (either treated or untreated with HA as indicated). Media exchange occurred twice weekly, and the newly synthesized neocartilage was harvested at day 45, unless otherwise indicated. The rate of proteoglycan synthesis for freshly dissociated chondrocytes derived from young donor cartilage typically was 2 µg S-GAG/µg DNA per day or greater.

Expansion of Chondrocytes in Serum-Containing Medium

Freshly dissociated chondrocytes were seeded in the indicated medium containing ascorbate and genatamicin at a final density of 0.5 to 3×10$^4$/cm$^2$ using T-75 flasks purchased from Corning. The cultures were maintained for 21 days, with complete exchange of medium occurring twice per week. At culture day 21, chondrocytes were enzymatically dissociated (5-8 hrs) using the collagenase/hyaluronidase mixture described above. Total cell number and viability was estimated using Guava ViaCount™ fluorescent cell counting solution and a Guava Personal Cell Analysis system. Guava Viacount™ solution distinguishes viable and non-viable cells based on the differential permeability of a combination of DNA-binding dyes in the reagent.

Derivitization of Tissue Culture Polystyrene

The glycosaminoglycan hyaluronic acid was covalently linked to polystyrene culture dishes (6 well plates and 100 mm diameter dishes, Corning) or T75 and T150 flasks, also purchased from Corning, using the procedure defined in Example 2. Briefly, each dish was treated for 2 hr with concentrated sulfuric acid at 37° C., washed extensively with distilled deionized water and then treated with aqueous ammonium hydroxide (30%, v/v) at room temperature for 24 hr. The reactive polysulfonamide (on the plastic surface) was crosslinked to sodium hyaluronate (5 mg/mL; Hylumed Medical, Genzyme; Cambridge, Mass.) using an aqueous solution of 1-ethyl-3(3-dimethylaminopropyl) carbodiimide (25 mg/mL, Sigma). The plates were placed in a humidified atmosphere at 37° C. for 48 hrs. Underivatized HA was removed by aspiration, and the plates were washed extensively with distilled deionized water, followed by two washes with HL-1.

Assessment of Chondrocyte Phenotype-biochemical Analyses

The differentiation potential of expanded chondrocytes was assessed by measuring the total proteoglycan and collagen content of newly synthesized neocartilage matrix. Sulfated glycosaminoglycans, hydroxyproline and deoxyribonucleic acid content were measured using established spectrophotometric methods after papain digestion as described previously. (Farndale and Murray, 1986; Stegemann and Stalder, 1967).

Assessment of Chondrocyte Phenotype-morphological Analyses

Freshly isolated chondrocytes were first expanded on unmodified tissue culture plastic (Example 4 only) in HL-1 Complete Serum-free Medium containing the indicate cytokines, ascorbate and gentamicin. An equal volume of fully supplemented medium was added on day 3, with 50% exchange of medium every 3 to 4 days until harvest. Chondrocytes were dissociated using the collagenase/hyaluronidase mixture described above, and subsequently transferred to 35 mm polystyrene dishes that had been modified via covalent attachment of sodium HA as described above in Derivitization. These cells were expanded to day 10 at which time they were dissociated and viability characterized using Guava ViaCount reagents as described above. Morphological characterization was performed using a Nikon TMS light microscope outfitted with a Nikon CoolPix995 camera.

Assessment of Chondrocyte Phenotype-gene Expression Analyses

Neocartilage derived chondrocytes were harvested as indicated for total RNA extraction from disrupted cell pellets using Qbiogene RNApro Solution (Qbiogene Inc, Carlsbad, Calif.), followed by RNeasy Mini Kit (Qiagen Inc, Valencia, Calif.) column purification. Semi-quantitative RT-PCR was performed using 0.5 µg of RNA in a 25 µL reaction mixture with RNA specific primers and the EZ rTth RNA PCR Kit (Perkin Elmer/Applied Biosystems, Foster City, Calif.). All experiments were performed three times on individual donors.

Primers sets used for PCR were selected using the LaserGene PrimerSelect Software, (DNAStar Inc., Madison, Wis.). All PCR primers were designed such that PCR products amplified by a given primer were specific for the gene of interest. The following oligonucleotide primer pairs for human collagen 1A1, 2A1, 9A1, 11A1, aggrecan core protein, N-cadherin, SOX-9, B7-H1 and GAPDH were synthesized at Sigma Genosys (Woodlands, Tex.). Primer pairs are listed in Table V.

TABLE V

Primer Pairs Used for Gene Expression Profile Analysis

| Gene | GenBank ID Number | Name of Primer | Sequence of Primer | |
|---|---|---|---|---|
| Aggrecan core | NM_001135 | AGC1-2S | GAAACTTCAGACCATGACAACTC | (SEQ ID NO.1) |
| | | AGC1-2AS | ACCAGCAGCACTACCTCCTTC | (SEQ ID NO.2) |
| B7-H1 | NM_014143 | B7-H1-1S | GCTCTTGGTGCTGGCTGGTC | (SEQ ID NO.3) |
| | | B7-H1-1AS | TCAGATATACTAGGTGTAGGGAA | (SEQ ID NO.4) |
| B7-1 | NM_005191 | B7-1-6S | GCCATCAACACAACAGTTTCCCAA | (SEQ ID NO.5) |
| (CD80) | | B7-1-6AS | CAGGGCGTACACTTTCCCTTCTCAA | (SEQ ID NO.6) |

TABLE V-continued

Primer Pairs Used for Gene Expression Profile Analysis

| Gene | GenBank ID Number | Name of Primer | Sequence of Primer | |
|---|---|---|---|---|
| B7-2 | NM_006889 | B7-2-6S | CTCTCTGGTGCTGCTCCTCTGAA | (SEQ ID NO.7) |
| (CD86) | | B7-2-6AS | CTGTGGGCTTTTTGTGATGGATGATAC | (SEQ ID NO.8) |
| Col1A1 | NM_000088 | Col1A1-3S | CGAGGGCCAAGACGAAGACA | (SEQ ID NO.9) |
| | | Col1A1-3AS | CTTGGTCGGTGGGTGACTCTGA | (SEQ ID NO.10) |
| Col2A1 | NM_033150 | Col2A1-8S | CACCCTGAGTGGAAGAGTGGAGCTAC | (SEQ ID NO.11) |
| | | Col2A1-8AS | CAGTGTTGGGAGCCAGATTGTCA | (SEQ ID NO.12) |
| Col9A1 | X54412 | Col9A1-5S | AAGCACAACTCAGTGCCCCAACAAAAC | (SEQ ID NO.13) |
| | | Col9A1-6AS | ATCCCATCACGGCCATCACA | (SEQ ID NO.14) |
| Col11A1 | J04177 | Col11A1-2S | AAGCACAACTCAGTGCCCCAACAAAAC | (SEQ ID NO.15) |
| | | Col11A1-2AS | CTACCCGATGCCACTTCCCGTCAG | (SEQ ID NO.16) |
| GAPDH | NM_002046 | GAPDH-1S | GCAAATTCCATGGCACCGTCA | (SEQ ID NO.17) |
| | | GAPDH-1AS | CAGGGGTGCTAAGCAGTTGG | (SEQ ID NO.18) |
| N-cadherin | BC036470 | NCAD-1S | GGAAAAGTGGCAAGTGGCAGTAAAAT | (SEQ ID NO.19) |
| | | NCAD-1AS | CCGAGATGGGGTTGATAATGAAGATA | (SEQ ID NO.20) |
| SOX-9 | Z46629 | SOX9-1S | GTCAACGGCTCCAGCAAGAACAA | (SEQ ID NO.21) |
| | | SOX9-1AS | GCTCCGCCTCCTCCACGAA | (SEQ ID NO.22) |

Semi-quantitative RT-PCR was performed using 0.5 µg of total RNA with 1 µl Thermus Thermophilus Polymerase (2.5 U/µl), 0.75 µL of each 10 mM dNTP, 5 µL of 5×EZ RT-PCR Buffer, 2.5 µL of 25 mM Mn(OAc)$_2$, and 2 µL of 5 µM stocks (0.4 µM final conc.) of upstream and downstream primers in a total volume of 25 µl. The final concentration of Mn(OAc)$_2$ in the buffer was 2.5 mM. The solutions were denatured at 94° C. for 1 minute prior to RT-PCR amplification using a programmable thermocycler (I-cycler, Bio-Rad Labs Inc., Hercules, Calif.) under the following conditions: Denaturation, 94° C. for 1 min., reverse transcriptase reaction at 58° C. for 30 min., followed by denaturation at 94° C. for 1 min., then PCR Cycling with 94° C. denaturation for 45 sec., and annealing and extension at 58° C. for 1 min. 10 seconds, for a total of 42 cycles. A final extension at 58° C. for 8 min. was performed, and the reaction products were stored at –80° C. PCR products were separated by electrophoresis on 2.5% agarose gels containing ethidium bromide. Gels were run at 80 V for approximately 90 min and photographed under UV light. Each experiment was performed a minimum of three times to confirm reproducibility.

Statistics

Prism software (version 3.0), manufactured by Graph Pad Software (San Diego, Calif.), was used to create graphic data. Data are presented as the mean±SD with replicates of three to five. Significance between groups was determined using the statistical package within the Prism suite.

EXAMPLE 8

Adult Chondrocytes Expanded on Hyaluronate Modified Substrata Show Enhanced Matrix Formation Potential.

This example demonstrates that adult chondrocytes expanded on an HA-modified substratum in defined medium significantly increased matrix formation of the expanded cells by greater than four-fold.

Chondrocytes derived from the articular cartilage of a 47 year-old male were expanded in HL-1 Complete Serum-free medium containing 100 ng/mL FGF-2 and 20 ng/mL TGF-β1, 50 µg/mL gentamicin and 50 µg/mL ascorbic acid. Two million cells were seeded into 100 mm diameter plates that had been modified by covalent attachment of sodium hyaluronate. Expansion cultures were maintained for a total of 17 days as described above (at each passage). Chondrocytes were subsequently released from the culture surface using a combination of collagenase/hyaluronidase, washed in HL-1 medium and total cell number and viability were measured using Guava Viacount reagents.

A portion of the first passage cells were placed into differentiation culture as described above to measure matrix formation potential for comparison with neocartilage produced from primary cells (FIG. 11). Two additional 100 mm diameter plates were set up (2 million cells per plate) for serial expansion to passage two, and the matrix formation potential of these expanded cells was assayed using the same method. Under these conditions, passage one and two cells demonstrated 3 and 2.7 population doublings, respectively, resulting in a cumulative increase of nearly 64-fold at day 34 of culture. The biochemical composition of newly synthesized neocartilage matrix produced (at day 45) from both the freshly isolated and expanded cells is shown in FIG. 11. The standard assay compared matrix formation in Medium A containing vitamin C, whereas two additional groups of cells (primary culture alone) were grown in Medium A that was further supplemented with dexamethasone 21-phosphate ($10^{-8}$ M; Sigma) or a combination of dexamethasone and FGF-2 (10 ng/mL).

Each population of expanded cells produced neocartilage that contained four-fold greater levels of sulfated glycosaminoglycans than the freshly isolated cells derived from the same donor (FIG. 11). The level of proteoglycan synthesis in the expanded cells was indistinguishable from that of primary cells that had been maintained in Media A containing dexamethasone alone or the combination of basic FGF and dexamethasone. These data show that expansion of adult chondrocytes on HA-modified substrata maintains the full differentiation potential of adult chondrocytes.

Other Embodiments

As various changes could be made in the above constructions without departing from the scope of the invention, it is intended that all matter contained in the above description or shown in the accompanying drawings shall be interpreted as illustrative and not in a limiting sense. Indeed, various modifications of the invention in addition to those shown and described herein will become apparent to those skilled in the art from the foregoing description which does not depart from the spirit or scope of the present inventive discovery. Such modifications are also intended to fall within the scope of the appended claims.

References Cited

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

REFERENCES CITED

U.S. Patent Documents

| | | | |
|---|---|---|---|
| 6235316B1 | May 22, 2001 | Adkisson | 424/548 |
| 6582960 | Jun. 24, 2003 | Martin et al. | 435/377 |
| 6617161 | Sep. 9, 2003 | Luyten et al. | 435/375 |
| 6645764B1 | Nov. 11, 2003 | Adkisson | 435/375 |
| 5830741 | Nov. 3, 1998 | Dwulet et al. | 435/220 |
| 5716404 | Feb. 10, 1998 | Vacanti et al. | 623/8 |
| 5753485 | May 19, 1998 | Dwulet et al. | 435/220 |
| 4356261 | Oct. 26, 1982 | Kuettner | 435/68 |
| 2003/0215426A1 | Nov. 20, 2003 | French et al. | 424/93.7 |

Other References

Adkisson et al., "In vitro generation of scaffold independent neocartilage", Clin. Orthop., vol. 391S, pp. S280-S294 (2001).

Benya and Shaffer, "Dedifferentiated Chondrocytes Reexpress the Differentiated Collagen Phenotype when Cultured in Agarose Gels", Cell, vol. 30, pp. 215-224 (1982).

Dell'Accio et al., "Molecular markers predictive of the capacity of expanded human articular chondrocytes to form stable cartilage in vivo", Arthritis & Rheumatism, vol. 44, pp. 1608-1619 (2001).

Farndale and Murray, "Improved quantization and discrimination of sulphated glycosaminoglycans by use of dimethylmethylene blue" Biochem. Biophys. Acta., vol. 883, pp. 173-177 (1986).

Hauselmann et al., "Phenotypic stability of bovine articular chondrocytes after long-term culture in alginate beads", J. Cell Science, vol. 107, pp. 17-27 (1994).

Hauselmann et al., "Adult human chondrocytes cultured in alginate form a matrix similar to native human articular cartilage", Am. J. Physiol., vol. 271, pp. C742-C752 (1996).

Homicz et al., "Effects of serial expansion of septal chondrocytes on tissue engineered neocartilage production", Otolaryngol. Head Neck Surg., vol. 127, pp. 398-408 (2002).

Huang et al., "Chondrogenic potential of multipotential cells from human adipose tissue", Plastic and Reconstructive Surgery, vol. 113, pp. 585-594 (2004).

Hunziker, "Articular cartilage repair: Basic science and clinical progress. A review of the current status and prospects", OsteoArthritis and Cartilage, vol. 10, pp. 432-463 (2002).

Jakob et al., "Specific growth factors during the expansion and redifferentiation of adult human articular chondrocytes enhance chondrogenesis and cartilaginous tissue formation in vitro", J. Cell. Biol., vol. 81, pp. 368-377 (2001).

Kavalkovick et al., "Chondrogenic differentiation of human mesenchymal stem cells within an alginate layer culture system", In Vitro Cell. Dev. Biol.-Animal, vol. 38, pp. 457-466 (2002).

Kogler et al., "A new human somatic stem cell from placental cord blood with intrinsic pluripotent differentiation potential", J. Exp. Med., vol. 200, pp. 123-135 (2004).

Kujawa et al, "Hyaluronic acid bonded to cell-culture surfaces stimulates chondrogenesis in stage 24 limb mesenchyme cell cultures", Dev. Bio., vol. 114, pp. 504-18 (1986).

Kujawa et al., "Substrate-bonded hyaluronic acid exhibits a size-dependent stimulation of chondrogenic differentiation of stage 24 limb mesenchymal cells in culture", Dev. Bio., vol. 114, pp. 519-28 (1986).

Kujawa et al., "Hyaluronic acid bonded to cell culture surfaces inhibits the program of myogenesis", Dev. Bio., vol. 113, pp. 10-16 (1986).

Laurent, "Structure of hyaluronic acid. In: the chemistry and molecular biology of the intercellular matrix, (Balazs ed.), vol. 2, pp. 703-732, Academic Press, New York (1970).

Laurent and Fraser, "Hyaluronan", FASEB J., vol. 6, pp. 2397-2404 (1992).

Liu et al., "An osteoconductive collagen/hyaluronate matrix for bone regeneration", Biomaterials, vol. 20, pp. 1097-1108.

Mackay et al., "Chondrogenic differentiation of cultured human mesenchymal stem cells from marrow" Tissue Eng., vol. 4, pp. 415-428 (1998).

Malpeli et al., "Serum-free growth medium sustains commitment of human articular chondrocyte through maintenance of Sox9 expression", Tiss. Eng., vol. 10, pp. 145-155 (2004).

Mandl et al., "Serum-free medium supplemented with high concentrations of FGF-2 for cell expansion culture of human ear chondrocytes promotes redifferentiation capacity" Tiss. Eng., vol. 4, pp. 573-580 (2002).

Mandl et al., "Multiplication of human chondrocytes with low seeing densities accelerates cell yield without losing redifferentiation capacity", Tiss. Eng., vol. 10, pp. 109-118 (2004).

Ornitz and Itoh, "Fibroblast growth factors", Genome Biol., vol. 2(3), pp. 3005.1-3005.12 (2001).

Ornitz, "FGFs, heparan sulfate and FGFRs: complex interactions essential for development", BioEssays, vol. 22, pp. 108-112 (2000).

Osman et al., "Combined transgenic expression of α-galactosidase and 1,2-fucosyltransferase leads to optimal reduction in the major xenoepitope Galα/(1,3) Gal", Proc. Natl. Acad. Sci., vol. 94, pp. 14677-14682 (1997).

Plotnikov et al., "Crystal structures of two FGF-FGFR complexes reveal the determinants of ligand-receptor specificity", Cell, vol. 101, pp. 413-424 (2000).

Reginato et al., "Formation of nodular structures resembling mature articular cartilage in long-term primary cultures of human fetal epiphyseal chondrocytes on a hydrogel substrate", Arthritis & Rheumatism, vol. 37, pp. 1338-1349 (1994).

Sandrin et al., "Enzymatic remodeling of the carbohydrate surface of a xenogenic cell substantially reduces human antibody binding and complement-mediated cytolysis", Nature Med., vol. 1, pp. 1261-1267 (1995).

Sekiya et al., "Dexamethasone enhances SOX9 expression in chondrocytes", J. Endocrinol, vol. 169, pp. 573-579 (2001).

Singley and Solursh, "The spatial distribution of hyaluronic acid and mesenchymal condensation in the embryonic chick wing", Dev. Biol., vol. 84, pp. 102-120 (1981).

Stegmann and Stalder, "Determination of hydroxyproline", Clin. Chim. Acta, vol. 18, pp. 267-273 (1967).

Turley and Roth, "Spontaneous glycosylation of glycosaminoglycan substrates by adherent fibroblasts", Cell, vol. 17, pp. 109-115 (1979).

Vacanti, "Beyond Transplantation", Arch. Surg., vol. 123, pp. 545-549 (1998).

Vacanti et al., "Selective cell transplantation using bioabsorbable artificial polymers as matrices", J. Pediatr. Surg., vol. 23, pp. 3-9 (1998).

West et al., "Angiogenesis induced by degradation products of hyaluronic acid", Science vol. 228, pp. 1324-1326 (1985).

Yoon et al., "Maintenance of differentiated phenotype of articular chondrocytes by protein kinase C and extracellular signal-regulated protein kinase", Biochem. J., vol. 277, pp. 8412-8420 (2002).

What is claimed is:

1. A method for expanding a population of chondrocytes in which the chondrocytes retain a rounded morphology and hyaline cartilage gene expression, the method comprising:
culturing a population of chondrocytes on a substrate in a culture medium, wherein the culture medium comprises at least one cytokine and wherein the substrate comprises polystyrene and hyaluronic acid which are covalently bound to each other, wherein the population of chondrocytes can undergo at least 3.8 doublings while at least 50% of the cells retain rounded morphology and hyaline cartilage gene expression.

2. The method of claim 1, wherein the chondrocytes are synovial capsule chondrocytes or periosteum chondrocytes.

3. The method of claim 1, wherein the culture medium is a serum-free culture medium.

4. The method of claim 3, wherein the culture medium comprises FGF-2 and TGF-β[ ].

5. The method of claim 1, wherein the at least one cytokine displays FGF-2-like activity or TGF-β-like activity.

6. The method of claim 1, wherein the at least one cytokine is selected from the group consisting of FGF-2, FGF-9, FGF-18, TGF-β1, TGF-β2, TGF-β3 and a bone morphogenetic protein.

7. The method of claim 6, wherein the at least one cytokine comprises FGF-2 or TGF-β1.

8. The method of claim 1, wherein the chondrocytes are juvenile articular chondrocytes.

9. The method of claim 1, wherein the chondrocytes are adult articular chondrocytes.

10. The method of claim 1, wherein the culturing comprises plating the chondrocytes at a cell density of about $0.5 \times 10^4$ to about $3 \times 10^4$ cell/cm$^2$.

11. A cell culture comprising chondrocytes, a culture medium comprising at least one cytokine, and a substrate comprising polystyrene and hyaluronic acid which are covalently bound to each other, wherein the population of chondrocytes can undergo at least 3.8 doublings and at least 50% of the chondrocytes retain rounded cell morphology and hyaline cartilage gene expression.

12. A cell culture in accordance with claim 11, wherein the culture medium is a serum-free culture medium.

13. A cell culture in accordance with claim 11, wherein the at least one cytokine is FGF-2 or has FGF-2-like activity.

14. A cell culture in accordance with claim 11, wherein the at least one cytokine is TGF-β or has TGF-β-like activity.

15. A cell culture in accordance with claim 11, wherein the chondrocytes are human chondrocytes.

16. A cell culture in accordance with claim 11, wherein the chondrocytes are transgenic chondrocytes resistant to immune-mediated xenograft rejection.

* * * * *

UNITED STATES PATENT AND TRADEMARK OFFICE
CERTIFICATE OF CORRECTION

PATENT NO. : 7,273,756 B2
APPLICATION NO. : 10/956971
DATED : September 25, 2007
INVENTOR(S) : Huston Davis Adkisson and Curt L. Milliman It is certified that error appears in the above-identified patent and that said Letters Patent is hereby corrected as shown below:

In Other Publications, line 3 of the Dell'Accio et al. citation, after "Rheumatism," add --2001,--

Column 1
Line 9, "70NANB1H3027" should be changed to --70NANB1H3027.--

Column 2
Line 63, "in" should be changed to --*in*--
Line 64, "vivo" should be changed to --*vivo*--

Column 3
Line 41, "5,658, 582" should be changed to --5,658,582--
Line 47, "in vivo" should be changed to --*in vivo*--

Column 4
Line 16, "in" should be changed to --*in*--
Line 17, "vitro" should be changed to --*vitro*--
Line 34, "Turely" should be change to --Turley--

Column 7
Lines 34 and 57, "in vitro" should be changed to --*in vitro*--

UNITED STATES PATENT AND TRADEMARK OFFICE
CERTIFICATE OF CORRECTION

PATENT NO. : 7,273,756 B2
APPLICATION NO. : 10/956971
DATED : September 25, 2007
INVENTOR(S) : Huston Davis Adkisson and Curt L. Milliman It is certified that error appears in the above-identified patent and that said Letters Patent is hereby corrected as shown below:

Columns 9-10, replace Table II with the following:

TABLE II
Double-agents cross-linkers

| Agent | Reactive toward (X) | | | | | |
|---|---|---|---|---|---|---|
| | Amines | Sulf-hydryls | Carbo-hydrates | Photo-reactive | Carboxyls | Hydroxyl |
| p-Azidobenzoyl Hydrazide (ABH) | | | X | X | | |
| 3-[(2-Aminoethyl)dithio]propionic acid·HCl (AEDP) | X | | | | X | |
| N-[α-Maleimidoacetoxy] succinimide ester (AMAS) | X | X | | | | |
| N-5-Azido-2-nitrobenzoyloxysuccinimide (ANB-NOS) | X | | | X | | |
| N-[4-(p-Azidosalicylamido) butyl]-3'-(2'-pyridyldithio) propionamide (APDP) | | X | | X | | |
| p-Azidophenyl glyoxal monohydrate (APG) | | | | X | | |
| 4-[p-Azidosalicylamido butylamine (ASBA) | | | | X | X | |
| Bis-[β-(4-Azidosalicylamido)ethyl] disulfide (BASED) | | | | X | | |
| 1,4-Bis-maleimidobutane (BMB) | | X | | | | |
| Bis-Maleimidoethane (BMOE) | | X | | | | |
| N-β-Maleimidopropionic acid (BMPA) | X | X | | | | |
| N-[β-Maleimidopropionic acid] hydrazide·TFA (BMPH) | | X | X | | | |
| N-[β-Maleimidopropyloxy] succinimide ester (BMPS) | X | X | | | | |
| 1,8-Bis-Maleimidotriethyleneglycol (BM[PEO]₃) | | X | | | | |

UNITED STATES PATENT AND TRADEMARK OFFICE
CERTIFICATE OF CORRECTION

PATENT NO. : 7,273,756 B2  
APPLICATION NO. : 10/956971  
DATED : September 25, 2007  
INVENTOR(S) : Huston Davis Adkisson and Curt L. Milliman Page 3 of 10

It is certified that error appears in the above-identified patent and that said Letters Patent is hereby corrected as shown below:

Columns 11-12, replace the first section of Table II-continued with the following:

TABLE II-continued

| | Double-agents cross-linkers | | | |
|---|---|---|---|---|
| 1,11-bis-Maleimidotriethyleneglycol (BM[PEO]₃) | | X | | |
| Bis[2-Succinimidyloxycarbonyloxy)-ethylsulfone (BSOCOES) | X | | | |
| Bis[Sulfosuccinimidyl] suberate (BS3) | X | | | |
| 1,5-Difluoro-2,4-dinitrobenzene (DFDNB) | X | | | |
| Dimethyl adipimidate·2 HCl (DMA) | X | | | |
| Dimethyl pimelimidate·2 HCl (DMP) | X | | | |
| Dimethyl suberimidate·2 HCl (DMS) | X | | | |
| 1,4-Di[3'-(2'-pyridyldithio)-propionamido]butane (DPDPB) | | X | | |
| Disuccinimidyl glutarate (DSG) | X | | | |
| Dithiobis[succinimidyl propionate] (DSP) | X | | | |
| Disuccinimidyl suberate (DSS) | X | | | |
| Disuccinimidyl tartrate (DST) | X | | | |
| Dimethyl 3,3'-dithiobispropionimidate·2 HCl (DTBP) | X | | | |
| Dithio-bis-maleimidoethane (DTME) | | X | | |
| 3,3'-Dithiobis[sulfosuccinimidyl propionate] (DTSSP) | X | | | |
| 1-Ethyl-3-[3-dimethylaminopropyl] carbodiimide Hydrochloride (EDC) | X | | | X |
| Ethylene glycol bis[succinimidylsuccinate] (EGS) | X | | | |
| N-ε-Maleimidocaproic acid) (EMCA) | X | X | | |
| N-[ε-Maleimidocaproic acid]hydrazide (EMCH) | | X | X | |
| N-[ε-Maleimidocaproyloxy] succinimide ester (EMCS) | X | X | | |
| N-[γ-Maleimidobutyryloxy] succinimide ester (GMBS) | X | X | | |
| 1,6-Hexane-bis-vinylsulfone (HBVS) | | X | | |
| N-κ-Maleimidoundecanoic acid (KMUA) | | X | X | |
| N-[κ-Maleimidoundecanoic acid]hydrazide (KMUH) | | X | X | |
| Succinimidyl 4-[N-maleimidomethyl]-cyclohexane-1-carboxy-[6-amidocaproate] (LC-SMCC) | X | X | | |
| Succinimidyl 6-[3-(2-pyridyldithio)-proionamido]hexanoate (LC-SPDP) | X | X | | |
| m-Maleimidobenzoyl-N-hydroxysuccinimide ester (MBS) | X | X | | |

UNITED STATES PATENT AND TRADEMARK OFFICE
CERTIFICATE OF CORRECTION

PATENT NO. : 7,273,756 B2
APPLICATION NO. : 10/956971
DATED : September 25, 2007
INVENTOR(S) : Huston Davis Adkisson and Curt L. Milliman It is certified that error appears in the above-identified patent and that said Letters Patent is hereby corrected as shown below:

Columns 13-14, replace Table III with the following:

TABLE III
Single-agents cross-linkers

| Agent | Amines | Sulf-hydryls | Carbo-hydrates | Photo-reactive | Carboxyls | Hydroxyl |
|---|---|---|---|---|---|---|
| 4-[N-Maleimidomethyl] cyclohexane-1- carboxylhydrazide· ½ dioxane($M_2C_2H$) |  | X | X |  |  |  |
| 3-Maleimidophenyl boronic acid(MPBH) |  | X | X |  |  |  |
| Methyl N-succinimidyl adipate(MSA) | X |  |  |  |  |  |
| N-Hydroxysuccinimidyl-4-azidosalicylic acid(NHS-ASA) | X |  |  | X |  |  |
| 3[2-Pyridyldithio]propionl hydrazide(PDPH) |  | X | X |  |  |  |
| N-[p-Maleimidophenyl] isocyanate(PMPI) |  | X |  |  |  | X |
| N-Succinimidyl [4-azidophenyl]- 1,3'-dithiopropionate(SADP) | X |  |  | X |  |  |
| Sulfosuccinimidyl 2-[7-axido-4-methylcoumarin-3- acetamido]ethyl- 1,3'-dithiopropionate(SAED) | X |  |  | X |  |  |
| Sulfosuccinimidyl 2-[m-azido-o-nitro- benzamido]ethyl- 1,3'-dithiopropionate(SAND) | X |  |  | X |  |  |
| N-Succinimidyl 6- [4'-azido-2'-nitro- phenylamino] hexanoateSANPAH | X |  |  | X |  |  |
| Sulfosuccinimidyl-2-[p-azido- salicylamido]ethyl- 1,3'-dithiopropionate(SASD) | X |  |  | X |  |  |
| N-Succinimidyl S- acetylthioacetate(SATA) | X | X |  |  |  |  |
| N-Succinimidyl S- acetylthiopropionate(SATP) | X | X |  |  |  |  |
| Succinimidyl 3- [bromoacetamido] propionate(SBAP) | X | X |  |  |  |  |
| Sulfosuccinimidyl- [perfluoroazido- benzamido]-ethyl- 1,3'-dithiopropionate(SFAD) | X |  |  | X |  |  |
| N-Succinimidyl iodoacetate(SIA) | X | X |  |  |  |  |
| N-Succinimidyl[4- iodoacetyl] aminobenzoate(SIAB) | X | X |  |  |  |  |
| Succinimidyl 4-[N- maleimidomethyl]- cyclohexane-1- carboxylate](SMCC) | X | X |  |  |  |  |
| Succinimidyl 4-[p- maleimidophenyl] butyrate(SMPB) | X | X |  |  |  |  |
| Succinimidyl-6-[(b- maleimidopropionamido) hexanoate](SMPH) | X | X |  |  |  |  |
| 4-Succinimidyloxy carbonyl-methyl-α [2-pyridyldithio] toluene(SMPT) | X | X |  |  |  |  |

UNITED STATES PATENT AND TRADEMARK OFFICE
CERTIFICATE OF CORRECTION

PATENT NO. : 7,273,756 B2  
APPLICATION NO. : 10/956971  
DATED : September 25, 2007  
INVENTOR(S) : Huston Davis Adkisson and Curt L. Milliman Page 5 of 10

It is certified that error appears in the above-identified patent and that said Letters Patent is hereby corrected as shown below:

Columns 13-14, replace Table III with the following (continued):

| | | | | |
|---|---|---|---|---|
| N-Succinimidyl 3-[2-pyridyldithio] propionate(SPDP) | X | X | | |
| Bis[2- (Sulfosuccinimido oxycarbonyloxy)- ethyl]sulfone(Sulfo-BSOCOES) | X | | | |
| Disulfosuccinimidyl tartrate(Sulfo-DST) | X | | | |
| Ethylene glycol bis [sulfosuccinimidylsuccinate](Sulfo-EGS) | X | | | |
| N-[ε-Maleimidocaproyloxy]sulfosuccinimide ester(Sulfo-EMCS) | X | X | | |
| N-[γ-Maleimidobutyryloxy]sulfo-succinimide ester(Sulfo-GMBS) | X | X | | |
| N-Hydroxysulfosuccinimidyl-4-azidobenzoate(Sulfo-HSAB) | X | | X | |
| N-[κ-Maleimidoundecanoyloxy]-sulfosuccinimide ester(Sulfo-KMUS) | X | X | | |
| Sulfosuccinimidyl 6-[3'-(2-pyridyldithio)- propionamido]hexanoateSulfo-LC-SPDP | X | X | | |
| m-Maleimidobenzoyl-N-hydroxysulfo- succinimide ester(Sulfo-MBS) | X | X | | |
| Sulfosuccinimidyl [4-azidosalicylamido]- hexanoate(Sulfo-NHS-LC-ASA) | X | | X | |
| Sulfosuccinimidyl [4-azidophenyldithio]- propionate(Sulfo-SADP) | X | | X | |
| Sulfosuccinimidyl 6-[4'-azido-2'-nitro- phenylamino] hexanoate(Sulfo-SANPAH) | X | | X | |
| Sulfosuccinimidyl [4-iodoacetyl]aminobenzoate(Sulfo-SIAB) | X | X | | |
| Sulfosuccinimidyl 4-[N-maleimidomethyl]- cyclohexane-1- carboxylate(Sulfo-SMCC) | X | X | | |
| Sulfosuccinimidyl 4-[p-maleimidophenyl]- butyrate(Sulfo-SMPB) | X | X | | |
| Sulfosuccinimidyl-6-[α-methyl-α-(2- pyridyldithio) toluamido] hexanoate(Sulfo-LC-SMPT) | X | X | | |
| Sulfosuccinimidyl [2-6-(biotinamido)- 2-(p-azidobenzamido)- hexanoamido]ethyl- 1,3'- dithiopropionate(Sulfo-SBED) | X | | X | |
| N-Succinimidyl-[4- vinylsulfony] benzoate(SVSB) | X | X | | |
| N-[ε-Trifluoroacetylcaproyloxy] succinimide ester(TFCS) | X | | | X |
| β-[Tris (hydroxymethyl) phosphino]- propionic acid (betaine)(THPP) | X | | | |
| Tris-[2-maleimidoethyl] amine(TMEA) | | X | | |
| Tris-succinimidyl aminotriacetate(TSAT) | X | | | |

UNITED STATES PATENT AND TRADEMARK OFFICE
CERTIFICATE OF CORRECTION

PATENT NO. : 7,273,756 B2
APPLICATION NO. : 10/956971
DATED : September 25, 2007
INVENTOR(S) : Huston Davis Adkisson and Curt L. Milliman It is certified that error appears in the above-identified patent and that said Letters Patent is hereby corrected as shown below:

Columns 13-14, replace Table III with the following (continued):

| Agent | Cleavable by (O) | | | | Iodina-table | Latent functional group |
|---|---|---|---|---|---|---|
| | Thiol | Base | Periodate | Hydroxyl-amine | | |
| 4-[N-Maleimidomethyl] cyclohexane-1- carboxylhydrazide· ½ dioxane($M_2C_2H$) | | | | | N | |
| 3-Maleimidophenyl boronic acid(MPBH) | | | | | N | |
| Methyl N-succinimidyl adipate(MSA) | | | | | N | CO-OH |
| N-Hydroxysuccini midyl-4-azidosalicylic acid(NHS-ASA) | | | | | Y | |
| 3[2-Pyridyldithio]propionl hydrazide(PDPH) | O | | | | N | |
| N-[p-Maleimidophenyl] isocyanate(PMPI) | | | | | N | |
| N-Succinimidyl [4-azidophenyl]- 1,3'-dithiopropionate(SADP) | O | | | | N | |
| Sulfosuccinimidyl 2-[7-axido-4-methylcoumarin-3- acetamido]ethyl- 1,3'-dithiopropionate(SAED) | O | | | | N | |
| Sulfosuccinimidyl 2-[m-azido-o-nitro- benzamido]ethyl- 1,3'-dithiopropionate(SAND) | O | | | | N | |
| N-Succinimidyl 6- [4'-azido-2'-nitro- phenylamino] hexanoateSANPAH | | | | | N | |

UNITED STATES PATENT AND TRADEMARK OFFICE
CERTIFICATE OF CORRECTION

PATENT NO.        : 7,273,756 B2
APPLICATION NO.   : 10/956971
DATED             : September 25, 2007
INVENTOR(S)       : Huston Davis Adkisson and Curt L. Milliman It is certified that error appears in the above-identified patent and that said Letters Patent is hereby corrected as shown below:

Columns 15-16, replace Table III-continued with the following:

TABLE III-continued
Single-agents cross-linkers

| Name | C1 | C2 | C3 | C4 | C5 | C6 |
|---|---|---|---|---|---|---|
| Sulfosuccinimidyl-2-[p-azido- salicylamido]ethyl- 1,3'-dithiopropionate(SASD) | O | | | | Y | |
| N-Succinimidyl S- acetylthioacetate(SATA) | | | | | N | -SH |
| N-Succinimidyl S- acetylthiopropionate(SATP) | | | | | N | -SH |
| Succinimidyl 3- [bromoacetamido] propionate(SBAP) | | | | | N | |
| Sulfosuccinimidyl- [perfluoroazido- benzamido]-ethyl- 1,3'- dithiopropionate(SFAD) | O | | | | N | |
| N-Succinimidyl iodoacetate(SIA) | | | | | N | |
| N-Succinimidyl[4- iodoacetyl] aminobenzoate(SIAB) | | | | | N | |
| Succinimidyl 4-[N- maleimidomethyl]- cyclohexane-1- carboxylate](SMCC) | | | | | N | |
| Succinimidyl 4-[p- maleimidophenyl] butyrate(SMPB) | | | | | N | |
| Succinimidyl-6-[(ß- maleimidopropionamido) hexanoate](SMPH) | | | | | N | |
| 4-Succinimidyloxy carbonyl-methyl-α [2-pyridyldithio] toluene(SMPT) | O | | | | N | |
| N-Succinimidyl 3-[2-pyridyldithio] propionate(SPDP) | O | | | | N | |
| Bis[2- (Sulfosuccinimido oxycarbonyloxy)- ethyl]sulfone(Sulfo-BSOCOES) | | O | | | N | |
| Disulfosuccinimidyl tartrate(Sulfo-DST) | | | O | | N | |
| Ethylene glycol bis [sulfosuccinimidylsuccinate](Sulfo-EGS) | | | | O | N | |
| N-[ε-Maleimidocaproyloxy]sulfosuccinimide ester(Sulfo-EMCS) | | | | | N | |
| N-[γ-Maleimidobutyryloxy]sulfo-succinimide ester(Sulfo-GMBS) | | | | | N | |
| N-Hydroxysulfosuccinimidyl-4-azidobenzoate(Sulfo-HSAB) | | | | | N | |
| N-[κ-Maleimidoundecanoyloxy]-sulfosuccinimide ester(Sulfo-KMUS) | | | | | N | |
| Sulfosuccinimidyl 6-[3'-(2-pyridyldithio)- propionamido]hexanoateSulfo-LC-SPDP | O | | | | N | |

UNITED STATES PATENT AND TRADEMARK OFFICE
CERTIFICATE OF CORRECTION

PATENT NO. : 7,273,756 B2
APPLICATION NO. : 10/956971
DATED : September 25, 2007
INVENTOR(S) : Huston Davis Adkisson and Curt L. Milliman It is certified that error appears in the above-identified patent and that said Letters Patent is hereby corrected as shown below:

Columns 15-16, replace Table III-continued with the following (continued):

| | | |
|---|---|---|
| m-Maleimidobenzoyl-N-hydroxysulfo- succinimide ester(Sulfo-MBS) | | N |
| Sulfosuccinimidyl [4-azidosalicylamido]- hexanoate(Sulfo-NHS-LC-ASA) | Y | |
| Sulfosuccinimidyl [4-azidophenyldithio]- propionate(Sulfo-SADP) | O | N |
| Sulfosuccinimidyl 6-[4'-azido-2'-nitro- phenylamino] hexanoate(Sulfo-SANPAH) | | N |
| Sulfosuccinimidyl [4-iodoacetyl]aminobenzoate(Sulfo-SIAB) | | N |
| Sulfosuccinimidyl 4-[N-maleimidomethyl]- cyclohexane-1- carboxylate(Sulfo-SMCC) | | N |
| Sulfosuccinimidyl 4-[p-maleimidophenyl]- butyrate(Sulfo-SMPB) | | N |
| Sulfosuccinimidyl-6-[α-methyl-α-(2- pyridyldithio) toluamido] hexanoate(Sulfo-LC-SMPT) | O | N |
| Sulfosuccinimidyl [2-6-(biotinamido)- 2-(p-azidobenamido)- hexanoamido]ethyl-1,3'-dithioproionate(Sulfo-SBED) | O | N |
| N-Succinimidyl-[4- vinylsulfony] benzoate(SVSB) | | N |
| N-[ε-Trifluoroacetylcaproyloxy] succinimide ester(TFCS) | | NH$_2$ |
| β-[Tris (hydroxymethyl) phosphino]- propionic acid (betaine)(THPP) | | N |
| Tris-[2-maleimidoethyl] amine(TMEA) | | N |
| Tris-succinimidyl aminotriacetate(TSAT) | | N |

UNITED STATES PATENT AND TRADEMARK OFFICE
CERTIFICATE OF CORRECTION

PATENT NO. : 7,273,756 B2
APPLICATION NO. : 10/956971
DATED : September 25, 2007
INVENTOR(S) : Huston Davis Adkisson and Curt L. Milliman It is certified that error appears in the above-identified patent and that said Letters Patent is hereby corrected as shown below:

Column 18
Line 33, "37 degrees C" should be changed to --37° C--
Line 35, "CO.sub.2" should be changed to --$CO_2$--

Column 19
Line 21, "CO.sub.2" should be changed to --$CO_2$--
Line 46, "in vivo" should be changed to --*in vivo*--
Line 53, "ex vivo" should be changed to --*ex vivo*--

Column 20
Line 6, "ex" should be changed to --*ex*--
Line 7, "vivo" should be changed to --*vivo*--
Line 64, "in vitro" should be changed to --*in vitro*--

Column 21
Line 44, "in vitro" should be changed to --*in vitro*--
Line 64, "Turely" should be changed to --Turley--

Column 23
Line 14, "ex" should be changed to --*ex*--
Line 15, "vivo" should be changed to --*vivo*--

Column 24
Line 66, "in vitro" should be changed to --*in vitro*-- and "in vivo" should be changed to --*in vivo*--

Column 27
Line 5, "1xinsulin, transferrin, selenite" should be changed to --1x insulin-transferrin-selenite--
Line 6, "Sima" should be changed to --Sigma--

UNITED STATES PATENT AND TRADEMARK OFFICE
CERTIFICATE OF CORRECTION

PATENT NO. : 7,273,756 B2
APPLICATION NO. : 10/956971
DATED : September 25, 2007
INVENTOR(S) : Huston Davis Adkisson and Curt L. Milliman It is certified that error appears in the above-identified patent and that said Letters Patent is hereby corrected as shown below:

Column 28
Line 46, "B7-H1and" should be changed to --B7-H1 and--

Column 41
Claim 4, line 2, "TGF-β[ ]" should be changed to --TGF-β--

Column 42
Claim 10, line 3, "cell/cm$^2$ ." should be changed to --cell/cm$^2$.--
Claim 14, line 2, "TGF-βor" should be changed to --TGF-β or--

Signed and Sealed this

Eighth Day of April, 2008

JON W. DUDAS
*Director of the United States Patent and Trademark Office*